(12) United States Patent
Lashinski et al.

(10) Patent No.: US 11,241,309 B2
(45) Date of Patent: Feb. 8, 2022

(54) METHODS FOR DELIVERY OF HEART VALVE DEVICES USING INTRAVASCULAR ULTRASOUND IMAGING

(71) Applicant: BOSTON SCIENTIFIC SCIMED, INC., Maple Grove, MN (US)

(72) Inventors: Randall Lashinski, Windsor, CA (US); Kristian Kristoffersen, Redding, CA (US); Matthew Rust, Windsor, CA (US); Richard Glenn, Santa Rosa, CA (US); Michael Lee, Santa Rosa, CA (US); Patrick Macaulay, Windsor, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 327 days.

(21) Appl. No.: 16/431,806

(22) Filed: Jun. 5, 2019

(65) Prior Publication Data
US 2019/0321176 A1   Oct. 24, 2019

Related U.S. Application Data

(63) Continuation of application No. 15/280,004, filed on Sep. 29, 2016, now Pat. No. 10,335,275.
(Continued)

(51) Int. Cl.
*A61F 2/24*   (2006.01)
*A61B 8/08*   (2006.01)
(Continued)

(52) U.S. Cl.
CPC ............ *A61F 2/2427* (2013.01); *A61B 8/085* (2013.01); *A61B 8/0841* (2013.01); *A61B 8/0883* (2013.01); *A61B 8/12* (2013.01); *A61B 8/445* (2013.01); *A61B 17/064* (2013.01); *A61B 17/068* (2013.01); *A61F 2/2412* (2013.01); *A61F 2/2466* (2013.01); *A61B 2017/00309* (2013.01); *A61B 2017/00314* (2013.01); *A61B 2017/00327* (2013.01);
(Continued)

(58) Field of Classification Search
CPC .... A61F 2/2427; A61F 2/2466; A61F 2/2412; A61B 8/445; A61B 8/085; A61B 8/0841; A61B 8/0883; A61B 8/12; A61B 17/064; A61B 2017/0647; A61B 2017/0649
See application file for complete search history.

(56) References Cited

U.S. PATENT DOCUMENTS 7,187,964 B2 *   3/2007   Khoury ................ A61B 5/6855
                                                              600/509
7,534,204 B2      5/2009   Starksen et al.
(Continued)

*Primary Examiner* — Julian W Woo

(57) ABSTRACT

Methods related to delivery of various heart valve implants are described. The implant may be delivered using an ultrasound imaging delivery system. The ultrasound imaging delivery system may be used to deliver a variety of different devices, including mitral valve reshaping devices, mitral valve replacement valves, and others. A deployment catheter carrying an implant having a tissue anchor is advanced to a deployment site in a heart. An imaging element is positioned adjacent the implant and a relationship between the tissue anchor and an anatomical landmark in the heart is visualized. The implant is then attached by driving the tissue anchor into tissue in the heart.

20 Claims, 23 Drawing Sheets

Related U.S. Application Data

(60) Provisional application No. 62/234,592, filed on Sep. 29, 2015.

(51) Int. Cl.
    *A61B 8/00*          (2006.01)
    *A61B 8/12*          (2006.01)
    *A61B 17/068*       (2006.01)
    *A61B 17/064*       (2006.01)
    *A61B 17/00*        (2006.01)

(52) U.S. Cl.
    CPC ................ *A61B 2017/0647* (2013.01); *A61B 2017/0649* (2013.01); *A61F 2/2418* (2013.01)

(56) References Cited

U.S. PATENT DOCUMENTS

| | | |
|---|---|---|
| 7,860,555 B2 | 12/2010 | Saadat |
| 8,734,484 B2 * | 5/2014 | Ahlberg ................. A61F 2/246 |
| | | 606/216 |
| 9,095,277 B2 | 8/2015 | House et al. |
| 9,616,197 B2 | 4/2017 | Serina et al. |
| 9,872,769 B2 | 1/2018 | Gross et al. |

* cited by examiner

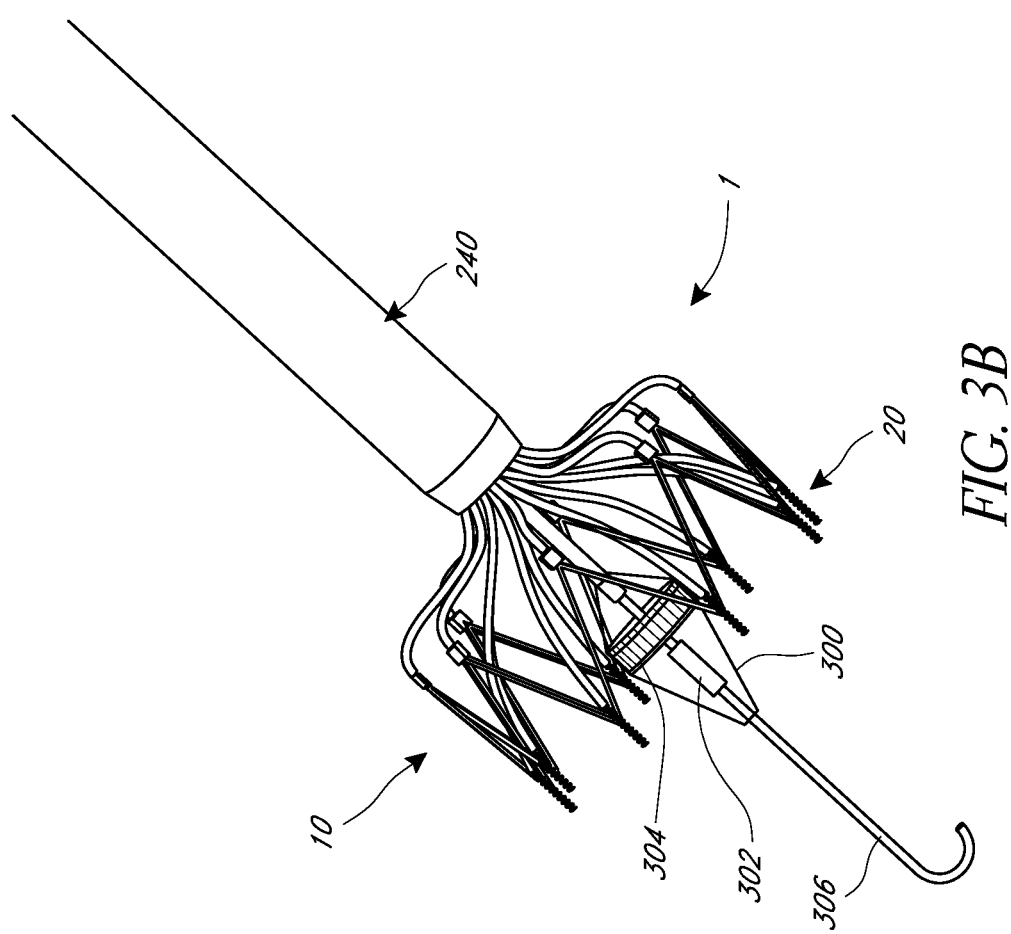

METHODS FOR DELIVERY OF HEART VALVE DEVICES USING INTRAVASCULAR ULTRASOUND IMAGING

INCORPORATION BY REFERENCE TO ANY PRIORITY APPLICATIONS

This application is a continuation of and claims priority to U.S. patent application Ser. No. 15/280,004, filed Sep. 29, 2016, which claims the benefit of priority 35 U.S.C. § 119 to U.S. Provisional Application Ser. No. 62/234,592 entitled "HEART VALVE DELIVERY SYSTEM WITH INTRAVASCULAR ULTRASOUND IMAGING CAPABILITY" and filed on Sep. 29, 2015, the entire disclosure of which are incorporated herein by reference in their entirety.

BACKGROUND

Field

In general, features related to systems and methods of delivering implantable medical devices are described. For example, delivery and positioning systems and methods for implanting various devices in a heart valve, for example to treat cardiac valve insufficiency, are described.

Description of the Related Art

Heart valve incompetency is a serious problem. For example, heart disease can cause the chambers of the heart to expand and weaken. With specific reference to the mitral valve, as a result of aging or disease, the left ventricle dilates and the papillary muscles are displaced. Consequently, the annulus of the mitral heart valve dilates excessively. In this state of dilation, valve leaflets no longer effectively close, or coapt, during systolic contraction. Consequently, regurgitation (i.e. retrograde flow back across the valve that should be closed) of blood occurs during ventricular contraction. Cardiac output is thus decreased.

This condition is typically addressed by the surgical implantation of an annuloplasty ring. A surgeon positions the annuloplasty ring proximate the valve annulus and sutures it in place thereby restoring the valve annulus to approximately its native configuration. The valve leaflets can now function normally again.

This procedure is invasive as it is performed open chest and is also time consuming. In open heart surgery, the patient is put on cardiopulmonary bypass with its associated risks of morbidity and mortality due to stroke, thrombosis, heart attack and extended recovery time.

There is, therefore, a need for less invasive and more efficient solutions to these problems that avoid the aforementioned drawbacks.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

Systems and methods of delivering a heart valve implant using ultrasound imaging are described. The implant is intended to be delivered in a minimally invasive percutaneous manner, such as transfemorally, transeptally, or transapically. The implant may instead be implanted surgically, in that it should reduce the duration of the procedure and, more particularly, the duration that the patient is on bypass. Furthermore, it should be recognized that the development can be directed to mitral valve or tricuspid valve procedures.

The development relates to the implant and delivery systems, and associated methods of use of each. The implant is a device capable of extending out to the dilated annulus of a heart valve, engaging the tissue of the heart valve annulus, and gathering or cinching it in to a smaller diameter. The implant includes a tubular frame with moveable struts, where pairs of adjacent struts form apexes. The apexes have collars at least partially surrounded the apex. After engaging heart valve annulus tissue with the implant, the collars can be moved down the apex to decrease the angle between the adjacent struts, causing the tubular frame to contract in width. This pulls the tissue of the heart valve annulus closer together. In some embodiments, the device has a ring-like member formed of a shape memory material that can be expanded, e.g. forcibly expanded, to engage and penetrate the tissue of the heart valve annulus. When the force is removed, the device moves, e.g. pulls, the tissue of the heart valve annulus tissue closer together. The implant thus reconfigures the valve annulus down to a smaller diameter, reducing and/or eliminating problems associate with the valve, such as regurgitation.

A delivery system and associated methods are also disclosed that comprise a delivery catheter comprising a proximal end, a distal end and a lumen extending from the proximal end to the distal end, the delivery catheter configured to transluminally position the distal end of the delivery catheter proximate to a valve annulus, an implant releasably coupled to the distal end of the delivery catheter, the implant comprising a frame defining an opening and at least one tissue anchor proximate to said opening, an imaging catheter comprising an imaging element at it distal end and an alignment mechanism coupled to the implant and to the imaging catheter and configured to position the imaging catheter relative to the implant for visualization during deployment. The delivery system can be used with the implant described herein as well as other implantable devices.

Moreover, the development also provides an artificial heart valve with a modified ring-like structure that not only provides for reduction of the heart valve annulus, but also displaces one or more defective heart valve leaflets. The artificial valve may include the various implant devices described herein having the one or more leaflets attached thereto.

In one aspect, a method of anchoring an implant in the heart is described. The method comprises advancing a deployment catheter to a deployment site in a heart, the deployment catheter releasably carrying an implant having at least one tissue anchor, positioning an imaging element in the heart adjacent the implant, visualizing a relationship between the tissue anchor and an anatomical landmark in the heart, and attaching the implant by driving the tissue anchor into tissue in the heart.

In some embodiments, the positioning an imaging element step comprises advancing the imaging element transvascularly along a same access path followed by the deployment catheter. In some embodiments, the positioning an imaging element step comprises advancing the imaging element through a lumen in the deployment catheter.

In some embodiments, the positioning an imaging element step comprises advancing the imaging element transvascularly along an access path that is different from an access path followed by the deployment catheter.

In some embodiments, the positioning an imaging element step comprises directing the imaging element to a predetermined relationship with the deployment catheter using an alignment structure. In some embodiments, the imaging element is carried by an imaging catheter and the positioning step comprises centering the imaging catheter within the implant using the alignment structure. In some embodiments, the centering step comprises inclining at least one alignment arm with respect to a longitudinal axis of the deployment catheter.

In some embodiments, the visualizing step comprises capturing at least one radial image. In some embodiments, the visualizing step comprises capturing at least one circumferential image. In some embodiments, the visualizing step comprises visualizing a heart valve annulus.

In some embodiments, the visualizing step comprises visualizing a Mitral valve annulus. In some embodiments, the attaching an implant step comprises attaching a Mitral valve annulus reshaping device. In some embodiments, the attaching an implant step comprises attaching a Mitral valve leaflet repair device. In some embodiments, the attaching an implant step comprises attaching a replacement Mitral valve.

In some embodiments, the attaching step comprises driving at least two anchors into tissue in the heart. In some embodiments, the attaching step comprises driving at least six anchors into tissue in the heart.

In some embodiments, the attaching step comprises rotating the anchor.

In some embodiments, the method further comprises the step of capturing a circumferential image following the attaching step. In some embodiments, the method further comprises the step of releasing the implant from the deployment catheter following the capturing a circumferential image step. In some embodiments, the method further comprises the step of manipulating at least one anchor following the capturing a circumferential image step.

In some embodiments, the visualizing step comprises capturing a field of view that includes at least a portion of the implant and of a Mitral valve leaflet.

In some embodiments, the deployment catheter has a central longitudinal axis and further comprising the step of deflecting the imaging element away from the central longitudinal axis. In some embodiments, the method comprises deflecting the imaging element in the direction of a tissue anchor.

In some embodiments, the method comprises capturing a first image of a first anchor, repositioning the imaging element, and capturing a second image of a second anchor. In some embodiments, the repositioning step comprises rotating the imaging element about an axis. In some embodiments, the repositioning step comprises rotating the imaging element about an axis using a rotational drive mechanism. In some embodiments, the repositioning step comprises manually rotating the imaging element about the axis.

In some embodiments, the imaging element is carried by an imaging catheter, further comprising locking a proximal engagement structure on the imaging catheter to a complementary engagement structure on the deployment catheter.

In another aspect, a method of delivering an implant proximate a cardiac valve annulus is described. The method comprises advancing a distal end of a delivery catheter proximate the cardiac valve annulus, advancing the implant through the distal end of the delivery catheter proximate the cardiac valve annulus, advancing a distal end of an ultrasound catheter proximate the cardiac valve annulus, the distal end of the ultrasound catheter including one or more ultrasonic transducers, capturing an ultrasound image of the implant and the cardiac valve annulus with the one or more ultrasonic transducers, and anchoring the implant to the cardiac valve annulus.

In some embodiments, the method further comprises rotating the distal end of the ultrasound catheter proximate the cardiac valve annulus to a plurality of rotational positions; and capturing a series of ultrasound images of the implant and the cardiac valve annulus with the one or more ultrasonic transducers at the plurality of rotational positions.

In some embodiments, the one or more ultrasonic transducers includes a radial ultrasonic transducer, and wherein capturing the series of ultrasound images comprises capturing one or more radial images of the implant and the cardiac valve annulus to properly position anchors of the implant for insertion into the cardiac valve annulus. In some embodiments, the one or more ultrasonic transducers includes a circumferential ultrasonic transducer, and wherein capturing the series of ultrasound images further comprises capturing one or more circumferential images of the implant and the cardiac valve annulus before anchoring the implant to the cardiac valve annulus. In some embodiments, the one or more ultrasonic transducers includes a circumferential ultrasonic transducer, and wherein capturing the series of ultrasound images further comprises capturing one or more circumferential images of the implant and the cardiac valve annulus after anchoring the implant to the cardiac valve annulus.

In some embodiments, the method comprises advancing the distal end of the delivery catheter proximate the cardiac valve annulus via the femoral vein or the iliac vein. In some embodiments, the method comprises advancing the distal end of the ultrasound catheter proximate the cardiac valve annulus through the delivery catheter. In some embodiments, the method comprises advancing the distal end of the ultrasound catheter proximate the cardiac valve annulus separately from the delivery catheter. In some embodiments, the method comprises advancing the distal end of the ultrasound catheter proximate the cardiac valve annulus through the aortic valve.

In some embodiments, the ultrasound catheter comprises a proximal end having a guidewire entry port, a distal end having a guidewire exit port, and a guidewire extending through the entry and exit ports.

In some embodiments, the ultrasound catheter is an intravascular cardiac echography (ICE) catheter.

In some embodiments, the method comprises centering the ultrasound catheter relative to the implant before capturing the ultrasound image and anchoring the implant. In some embodiments, the method comprises the ultrasound catheter is centered relative to the implant by coupling the implant with the ultrasound catheter via a plurality of radial arms of a centering frame that extend from the implant to the ultrasound catheter.

According to one aspect, an implant comprises a series of struts defining a tubular frame and an axis and forming a plurality of upper crowns and lower crowns, a plurality of anchors coupled with at least some of the plurality of lower crowns of the tubular frame and configured to translate axially relative to the tubular frame to engage cardiac tissue proximate the cardiac valve annulus and an alignment mechanism for an imaging catheter, coupled to the tubular frame and configured to position an imaging element of the imaging catheter at a predetermined location relative to the tubular frame.

In some embodiments, the implant is a cardiac valve replacement and comprises a series of struts defining a tubular frame and an axis and forming a plurality of lower crowns, a plurality of anchors coupled with the lower crowns of the frame and configured to translate axially relative to the frame to engage cardiac tissue proximate the cardiac valve annulus, and a plurality of valve leaflets coupled with the frame. In some embodiments, anchoring the implant to the cardiac valve annulus comprises rotating the plurality of anchors into the cardiac tissue. In some embodiments, the implant further comprises a housing coupled with the frame, and wherein the leaflets are coupled with the frame via the housing. In some embodiments, the implant further comprises a plurality of upper crowns defined by the series of struts, and a plurality of collars at least partially surrounding the upper crowns and configured to translate axially relative to the frame to adjust a width of the implant. In some embodiments, the implant further comprises an atrial flange.

According to one aspect, a cardiac valve implant delivery system comprises a delivery catheter comprising a proximal end, a distal end and a lumen extending from the proximal end to the distal end, the delivery catheter configured to transluminally position the distal end of the delivery catheter proximate to a cardiac valve annulus, an implant releasably coupled to the distal end of the delivery catheter, the implant comprising a tubular frame comprised of a series of struts joined to form a plurality of upper and lower crowns, a plurality of anchors coupled with the lower crowns of the tubular frame and configured to translate axially relative to the tubular frame to engage cardiac tissue proximate the cardiac valve, an imaging catheter comprising at least one imaging element rotatably disposed within the tubular frame; and an alignment mechanism coupled to the tubular frame and the imaging catheter and configured to position the imaging elements of the imaging catheter within the tubular frame to enable visualization of the plurality of anchors during deployment of a cardiac valve implant. In some embodiments, the cardiac valve annulus is a mitral valve annulus. In some embodiments, the cardiac valve annulus is a tricuspid valve annulus.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIGS. 3A-3D are perspective views of another embodiment of an ICE catheter and delivery system for delivering, e.g. aligning and positioning, an implant and having a circular array of sensors at the tip of the catheter, e.g. for radial and/or circumferential echo views.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

Various heart valve implants may be delivered proximate to, above and/or or within, the cardiac valve annulus. Unless otherwise stated, "valve" as used herein may refer to either the tricuspid or mitral valve of the heart. The implant may be subsequently implanted in the annular cardiac tissue just above the plane of the valve orifice. In some embodiments, the implant may be a heart valve replacement including valve leaflets, which can be implanted in annular cardiac tissue and extend into the valve annulus.

Particular features for various embodiments of an implant, of a delivery system, and of related systems and methods of use of the delivery system (either together or separately), are described herein. The implant, delivery system, and related systems and methods of use may have the same or similar features and/or functionalities as other implants, delivery systems, and related systems and methods of use as described, for example, in U.S. patent application Ser. No. 14/861,877 entitled "ADJUSTABLE ENDOLUMENAL IMPLANT FOR RESHAPING MITRAL VALVE ANNULUS and filed on Sep. 22, 2015, and as described, for example, in U.S. Provisional Application No. 62/234,592 entitled "HEART VALVE DELIVERY SYSTEM WITH INTRAVASCULAR ULTRASOUND IMAGING CAPABILITY" and filed on Sep. 29, 2015, the entire disclosure of each of which is incorporated herein by reference for all purposes and forms a part of this specification. Thus, the description of particular features and functionalities herein is not meant to exclude other features and functionalities, such as those described in the references incorporated herein by reference or others within the scope of the development.

Figure 1A:
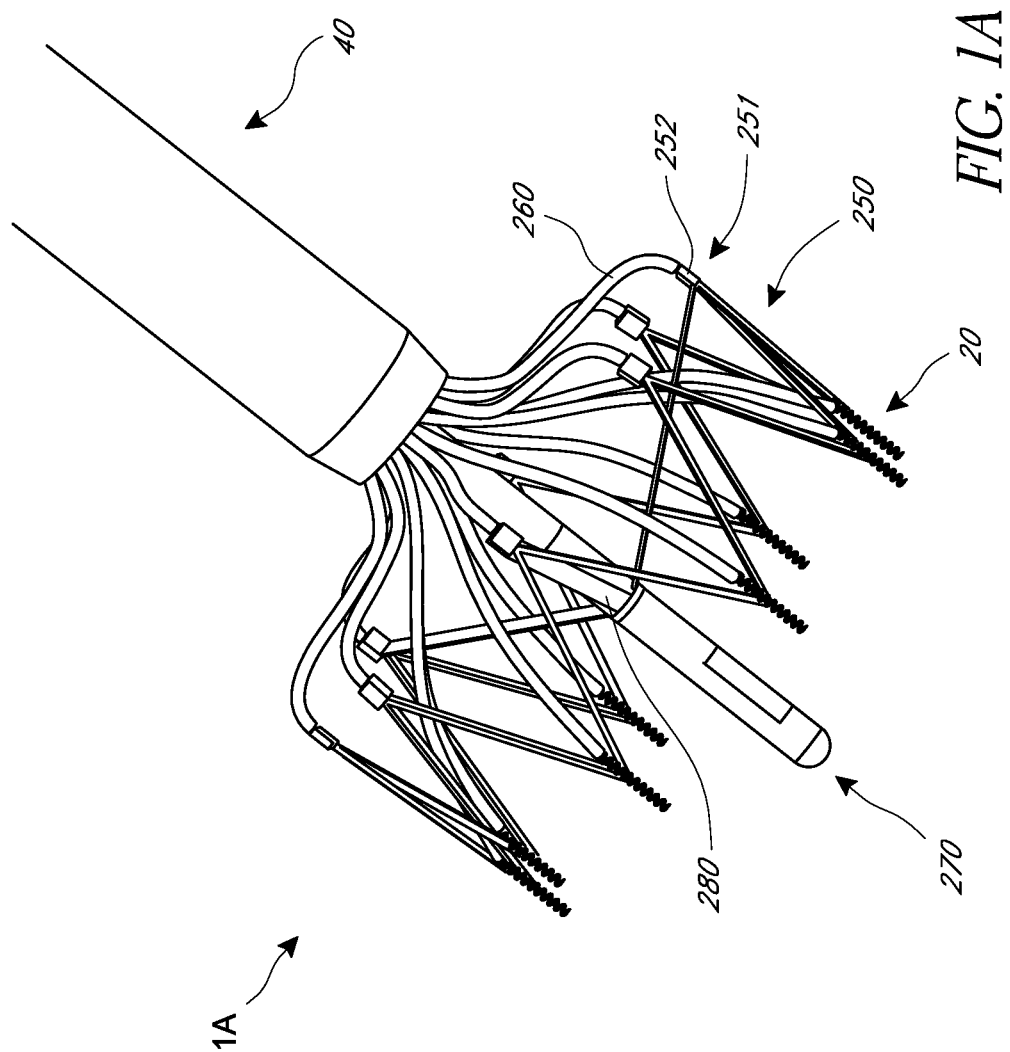
FIGS. 1A through 1E are perspective views of various embodiments of delivery catheters having positioning and imaging capabilities and delivering various embodiments of heart valve implants for resizing the native valve annulus.
Figure 1B:
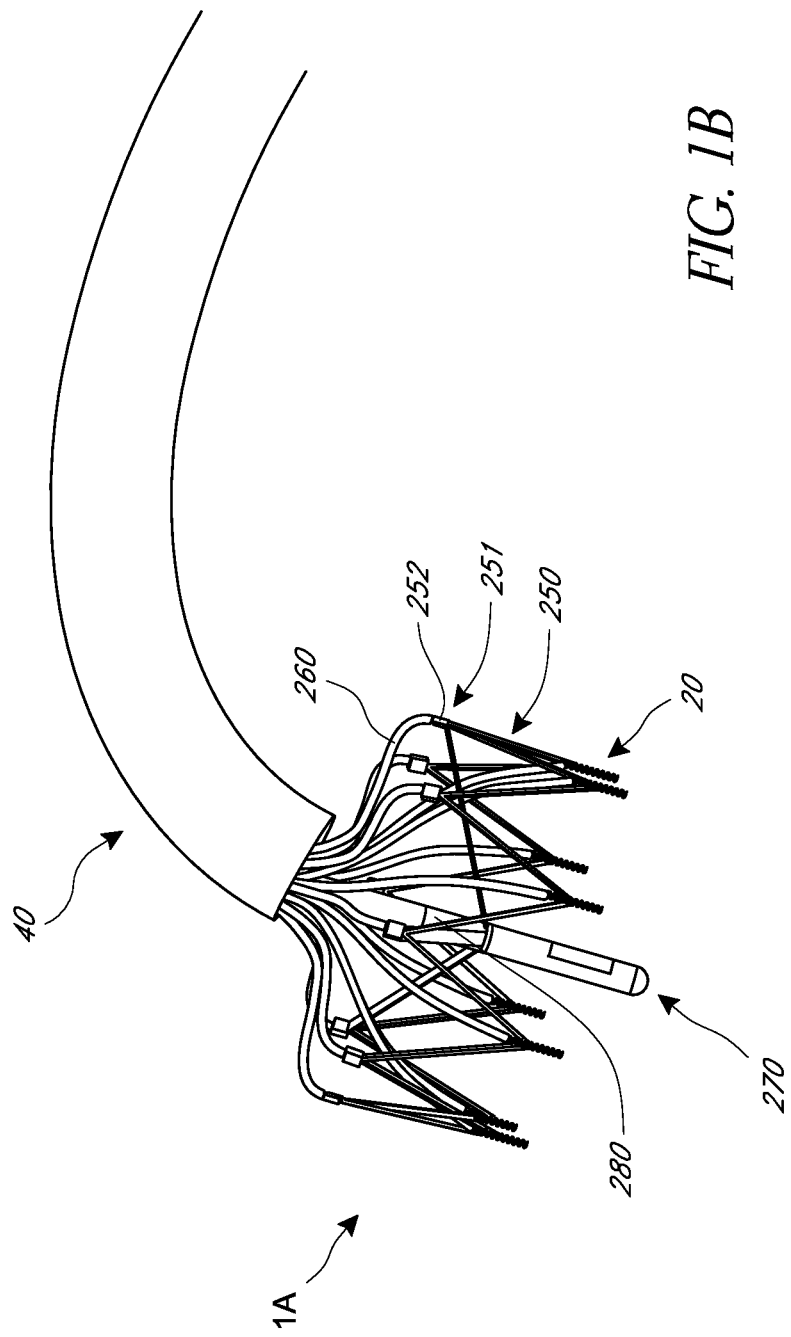

FIGS. 1A and 1B are perspective views of an embodiment of a distal end of a delivery catheter 40 that may be used to deliver various implants. The delivery catheter 40 has various positioning and imaging capabilities. The distal end of the delivery catheter 40 is maneuvered into position above the heart valve annulus. An implant 1A shown being delivered in FIGS. 1A-1B is for resizing the heart valve annulus. It is understood that a variety of different implants may be delivered with the delivery system and methods described herein. As shown, this particular implant includes a frame 250. The frame 250 has anchors 20 attached to a lower or distal portion of the frame 250 and extending distally therefrom. The frame 250 has an upper or proximal portion with collars 252 extending over upper crowns 251 of the frame 250. Only some of the collars 252, upper crowns 251 and anchors 20 are labelled for clarity. The collars 252 may be moved, e.g. distally, along the frame 250 by driver tubes 260 to resize the frame 250.

The frame 250, driver tubes 260, and an intravascular cardiac echography (or "ICE") catheter 270 may be extended from the distal end of the delivery catheter 40. The drive tubes 260 are shown engaging corresponding upper crowns 252 of the frame 250. A centering frame 280 maintains concentric positioning of the ICE catheter 270 relative to the frame 250 during deployment, alignment and positioning of the frame 250 above and proximate to the target heart valve annulus tissue. The centering frame 280 maintains a generally centered position of the catheter 270 relative to the frame 250. By centering the ICE catheter within the frame 250, the operator need only rotate the ICE catheter 270 to view each anchor 20 and placement of the anchors 20. Further, the ICE catheter 270 could be used to view various other individual features of the implant 1A, such as the collars 252, for instance to view the extent to which each collar 252 is advanced down and over upper crowns 251 of the frame 250, to more precisely adjust the size of the frame 250. The ICE catheter 270 could also provide significant benefit to an embodiment where a singular cinching mechanism or driver tube needs to be landed on each crown 251 of the frame 250 to adjust the sizing of the frame 250. An indexing feature (not shown) may also be provided on the ICE catheter 270, for example, such that actuation of the indexing feature by the operator causes the ICE catheter 270 to automatically move, or rotate, to the next anchor 20 position.

Figure 1C:
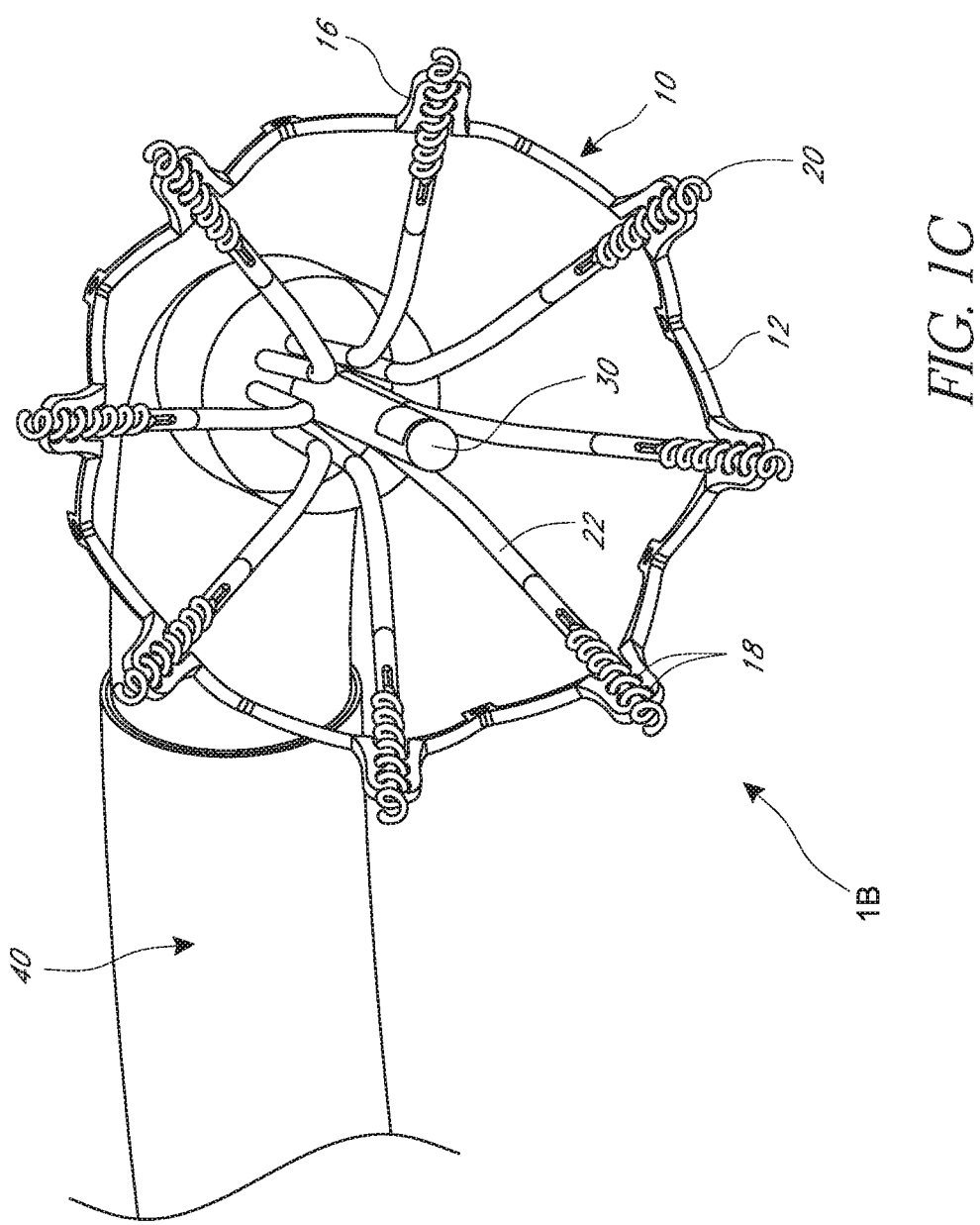
Figure 1D:
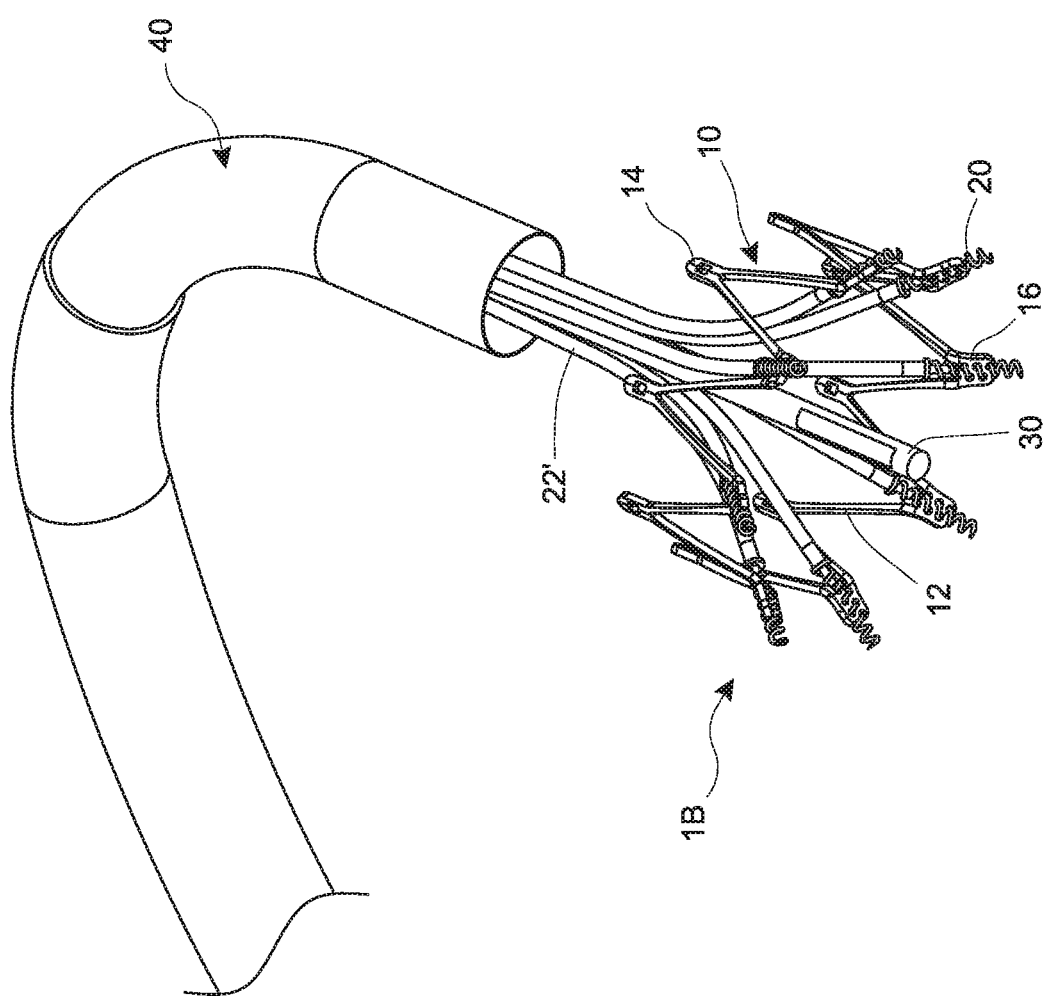

FIGS. 1C and 1D are perspective views of an embodiment of an implant 1B being delivered and implanted by the delivery catheter 40. The implant 1B may be analogous to the implant 1A. By "analogous" it is meant the two features may have the same or similar features and/or functionalities. As shown in FIGS. 1C and 1D, the implant 1B includes a frame 10 with struts 12 forming upper apexes or crowns 14 and lower apexes or crowns 16. The lower crowns 16 have openings 18, such as holes, aligned to receive the anchors 20 there through. For clarity, only some of the upper crowns 14, lower crowns 16, struts 12 and anchors 20 are labelled in FIGS. 1C and 1D. The anchors 20 may be rotated to move distally through the openings 18. The implant 1B is intended to be delivered proximate to and above a cardiac valve (tricuspid, mitral) annulus, and subsequently implanted in the annular cardiac tissue just above the plane of the valve orifice.

Driver tubes 22, having proximal portions 22' extending out of the delivery catheter 40, are provided for rotationally engaging the anchors 20. Manipulation, for example rotation, of the driver tubes 22 by the operator causes the anchors 20 to advance towards, engage with and penetrate cardiac tissue to secure frame 10 into the annulus approximate and above the valve. The anchors 20 may be advanced individually one at a time, some advanced together, or all advanced together. In some embodiments, the driver tube 22 may rotate relative to the proximal portion 22'. In some embodiments, the driver tube 22 and proximal portion 22' are part of the same, continuous driver tube and/or the entire tube 22 and 22' may rotate together.

An embodiment of an ultrasound catheter 30, such as the Acuson IPX8 AcuNav catheter, is shown contained within and advanced down a central lumen of the delivery catheter 40. The ultrasound catheter 30 may be analogous to the ICE catheter 270. In some embodiments, by rotating the ultrasound catheter 30 around the inside of the valve annulus, the relative position of the frame 10, and of any valve leaflets, will be seen for accurate positioning of the anchors 20 around and above the valve annulus.

In some embodiments, the ultrasound catheter 30 is contained within and advanced down an offset, non-central lumen of the delivery catheter 40. In this manner, the ultrasound catheter 30 would not interfere with the frame 10, its attachments or other features, and the driver components. In some embodiments, the ultrasound catheter 30 may be located and steered to the side of the annulus to image, allowing for less rotation to more quickly view the anchor points of the frame 10. An offset lumen could exit more proximally with regard to the distal end of the delivery catheter 40. This more proximal exit would reduce the overall profile or diameter of the distal end of the delivery catheter 40. In addition, this more proximal exit port would enable a view of the valve annulus from above. The offset lumen could also be compressible allowing for an even smaller profile until the ultrasound catheter 40 is advanced through the offset lumen.

While the ultrasound catheter 30 is shown integrated into the same delivery system as the delivery catheter 40, in some embodiments the ultrasound catheter 30 could otherwise be introduced secondarily through another entry site, such as through the aortic valve, and placed near or inside the implant for imaging and placement of the anchors 20.

Figure 1E:
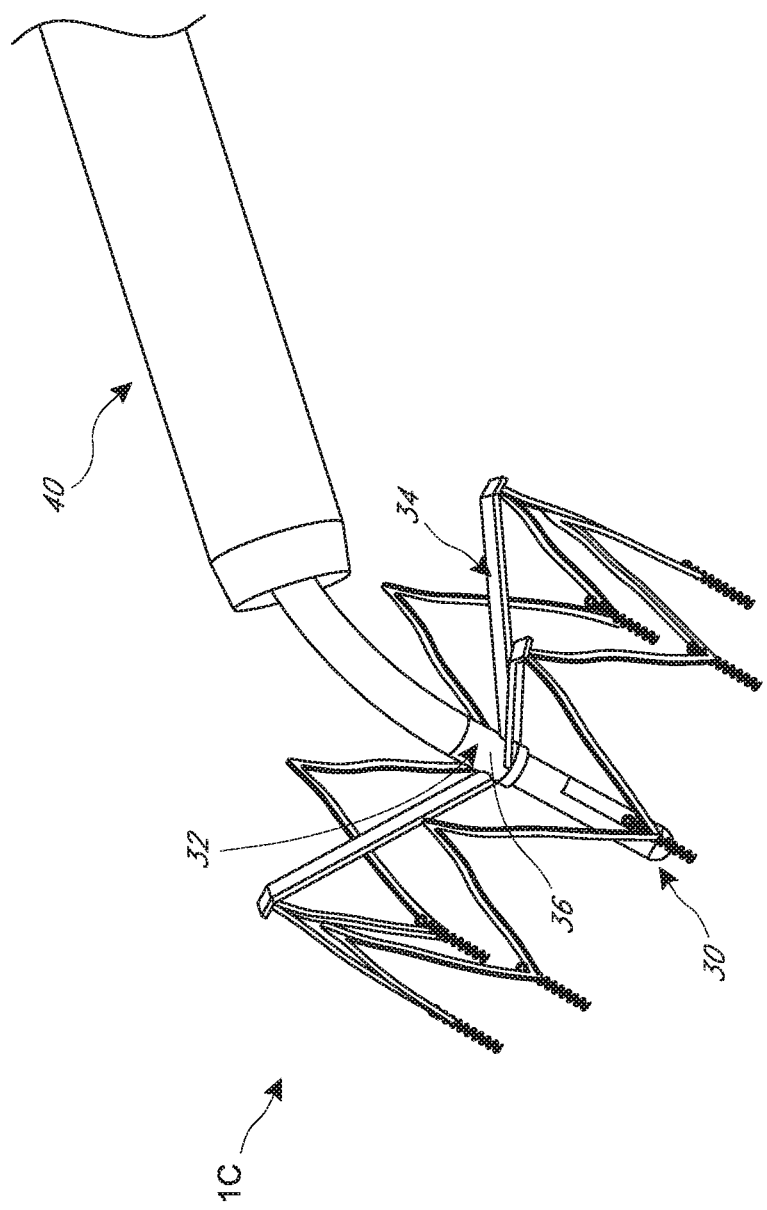

FIG. 1E is a perspective view of an embodiment of a centering frame 32 coupled to the ultrasound catheter 30 and to an implant 1C. The implant 1C may be analogous the implants 1A and 1B. The centering frame 32 has centering arms 34 connected to a centering hub 36 that is mounted on the ultrasound catheter 30. As the distal end of the delivery catheter 40 is maneuvered into position above the heart valve annulus, the centering frame 32 maintains concentric positioning of the ultrasound catheter 30 relative to the frame 10 during deployment, alignment and positioning of the frame 10 above and proximate to the target heart valve annulus tissue. The centering aspect is desirable, for example, because if the ultrasound catheter 30 remains centered within the frame 10, the operator such as a surgeon or technician need only rotate the ultrasound catheter 30 to view each anchor 20 and placement the of each anchor 20. There may also be an indexing feature (not shown) on the ultrasound catheter 30 such that actuation of the indexing feature by the operator causes the ultrasound catheter 30 to automatically move, or rotate, to the next anchor position. The centering frame 32 maybe used with delivery of the various implants described herein, such as the annulus resizing implants and/or the heart valve replacement implants.

Figure 2:
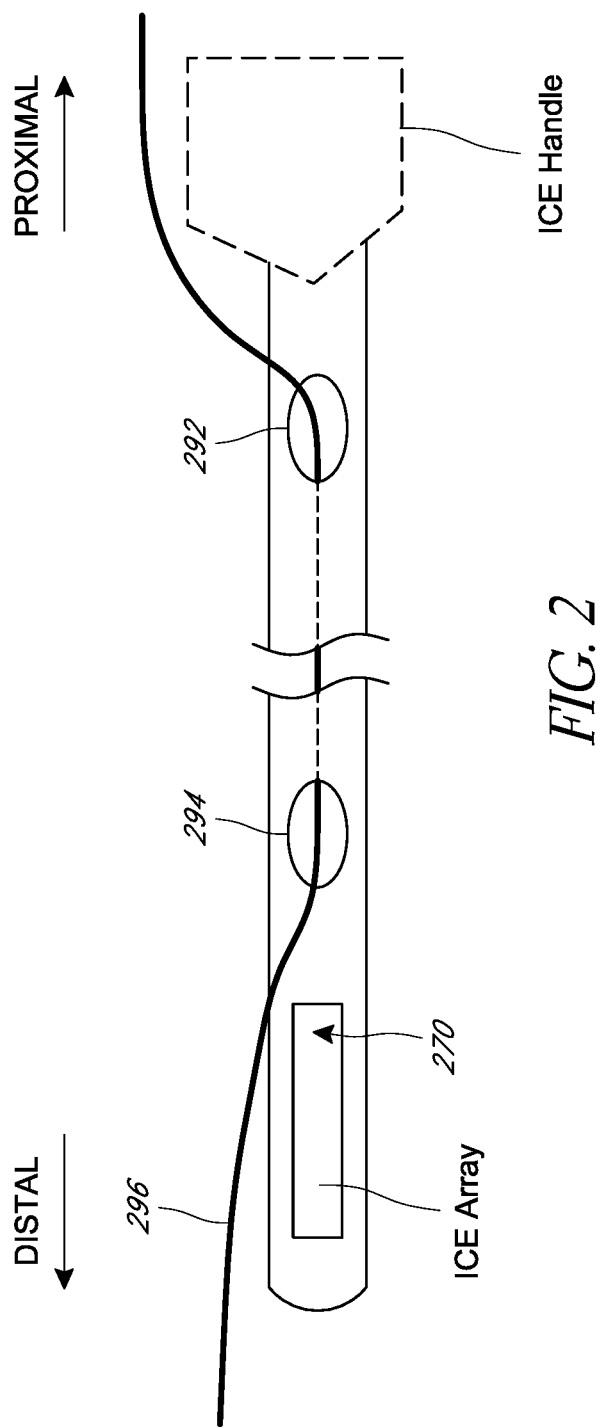
FIG. 2 is a side view of an embodiment of a modified intravascular cardiac echography (ICE) catheter for delivering, e.g. aligning and positioning, an implant and having a guidewire entering and exiting the catheter.

FIG. 2 is a side view of an embodiment of the ICE catheter 270. The ICE catheter 270 as shown includes a guidewire entry port 292 and a guidewire exit port 294 which together accept the guidewire 296. This embodiment allows the ICE catheter 270 to be delivered separately from the frame 10 thereby reducing the overall diameter of the delivery catheter 40 (e.g. as shown in FIGS. 1A and 1B). An ICE handle may be located at a proximal end of the catheter 270. An ICE array may be located at the distal end of the catheter 270.

In some embodiments, a separately delivered ultrasound catheter 270 could be functionally linked to the distal end of the delivery catheter 40 and to the inside of the frame 10. The delivery catheter 40 could have mechanical docking and radiopaque features to aid in delivery and stability of the ultrasound catheter 270 relative to the delivery catheter 40.

Figure 3A:
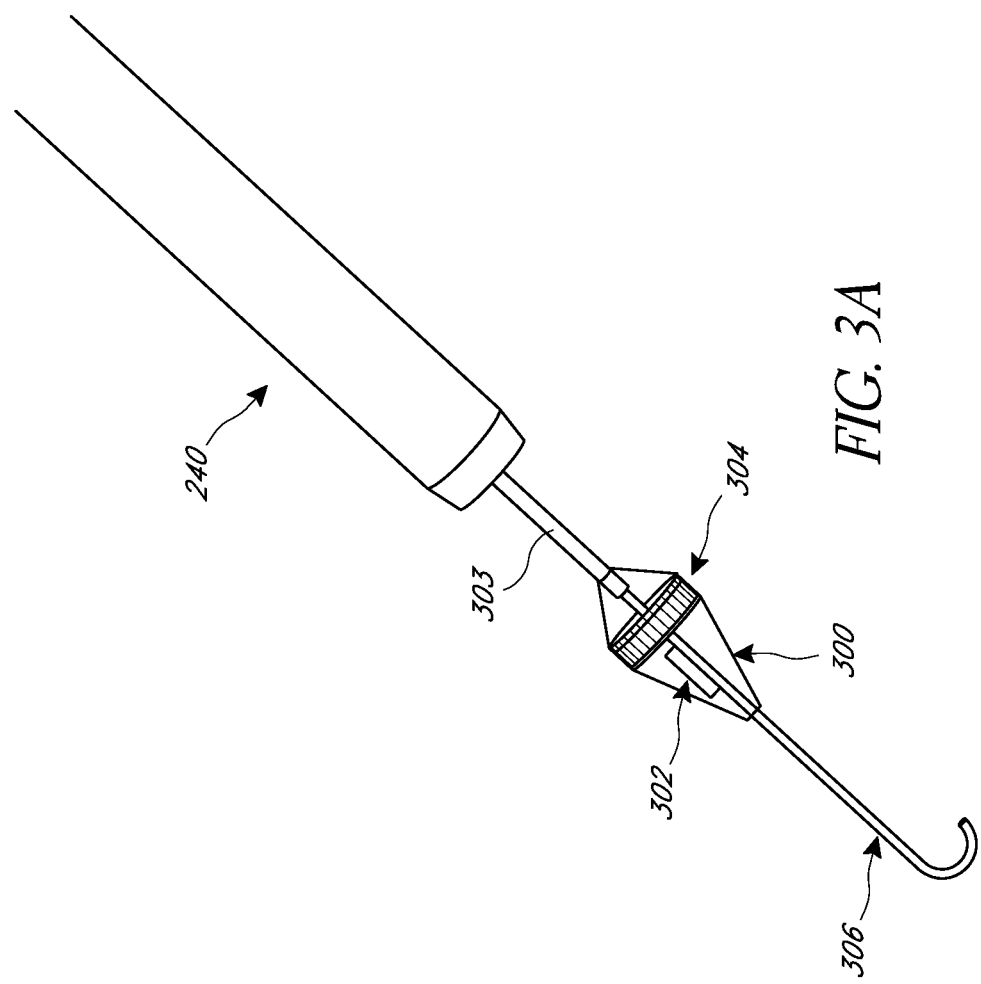
Figure 3C:
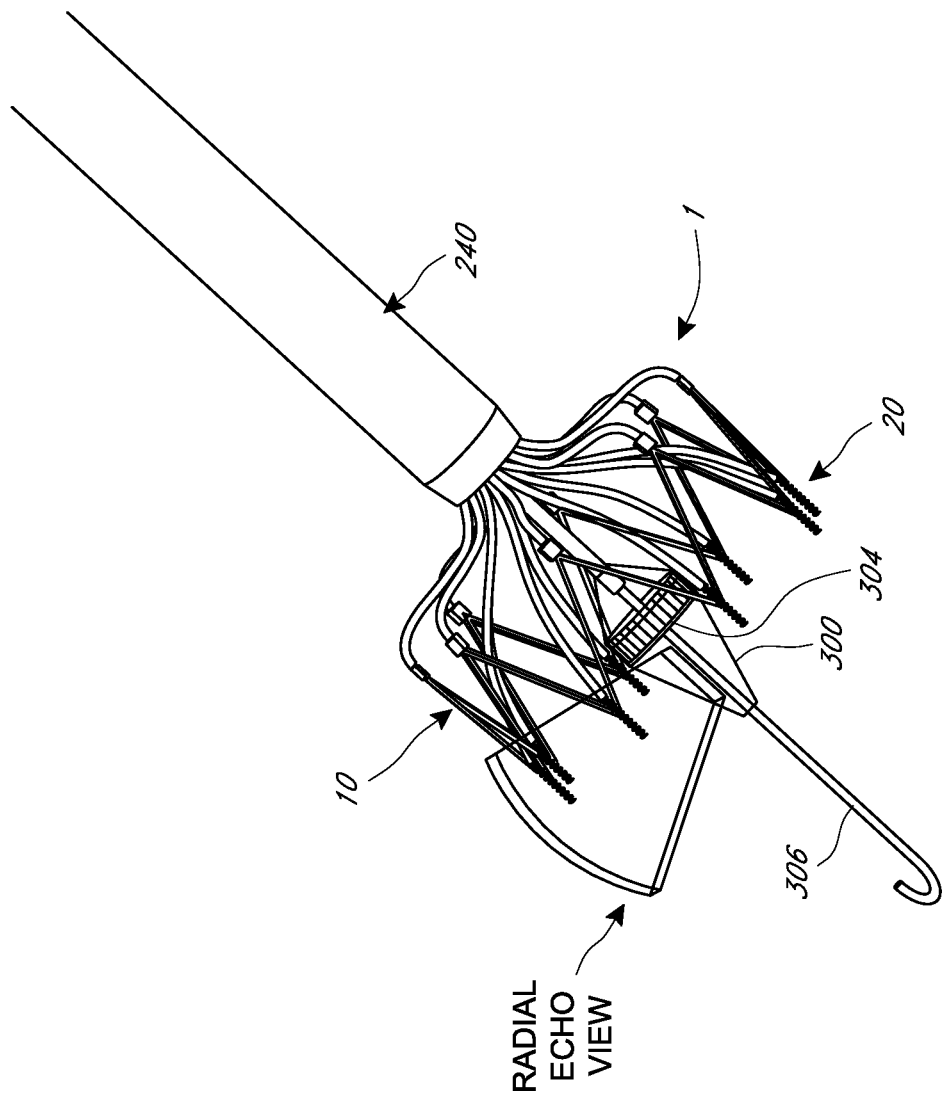
Figure 3D:
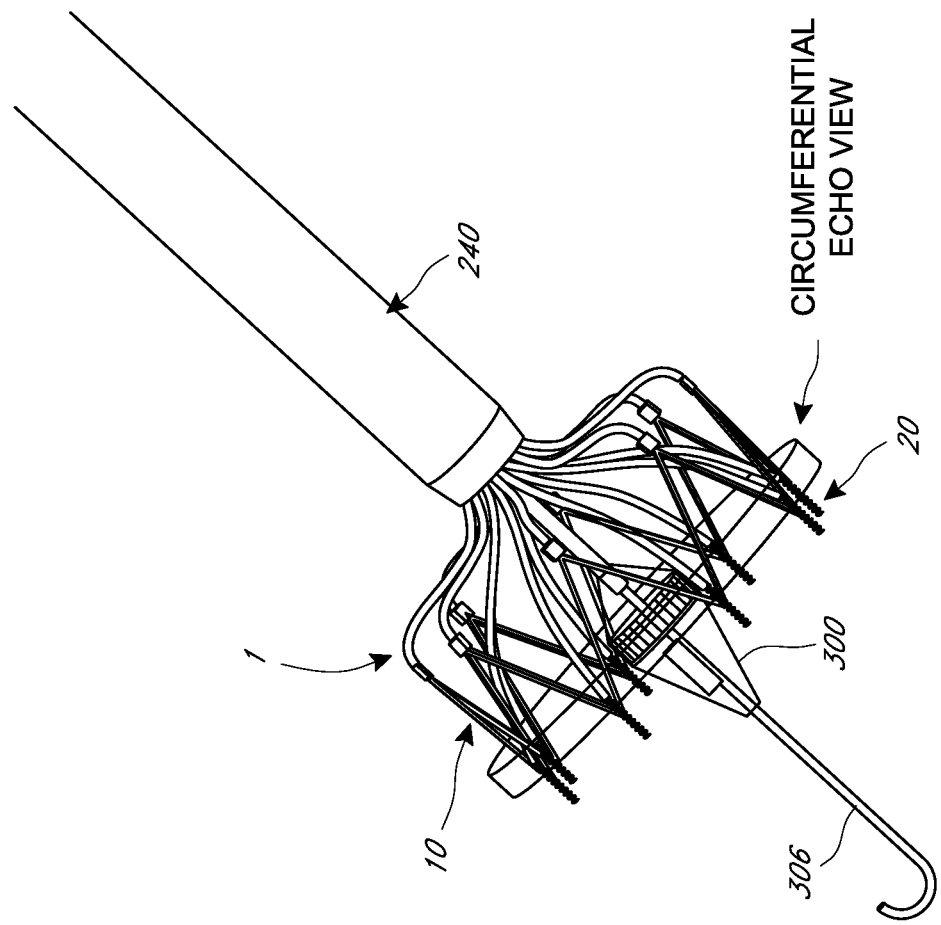

FIGS. 3A, 3B, 3C and 3D depict an embodiment of an ICE catheter 300 that may be used with the various implant and delivery devices, systems and methods described herein. The ICE catheter 300 has radial ultrasonic transducers 302, circumferential ultrasonic transducers 304 and guidewire 306 passing centrally therethrough. In some embodiments, there may be one or more radial ultrasonic transducer and/or one or more circumferential ultrasonic transducers. A guidewire lumen 303 extends out from a delivery catheter 240. The delivery catheter 240 may be analogous to the delivery catheter 40. The ICE catheter 300 extends out through the guidewire lumen 303. FIGS. 3B and 3C show an implant 1 deployed with the ICE catheter 300 tip. The implant 1 may be analogous to the implants 1A, 1B or 1C. FIG. 3C further shows the relationship of the ICE catheter 300 to the delivery catheter 240 while it is taking a radial echo view to properly position the anchor 20 for insertion into heart valve annulus tissue. FIG. 3D shows the ICE catheter 300 capturing a circumferential echo image for properly positioning the frame 10 in a plane above the heart valve and its leaflets. The features shown and described in FIGS. 3A-3D may be used to deliver various other implants, such as other resizing devices or heart valve replacement valves.

In some embodiments, software or electronic controls can be effective to cycle through the radial cross sectional images around the valve annulus perimeter, relieving the need to physically move, via rotation, translation or deflection, the ICE catheter 300. A larger circumferential transducer array could also be placed distal of the annulus to not interfere with space limitations of the delivery catheter 240, further decreasing the profile of the delivery catheter 240. In another embodiment, the transducers of the ICE catheter 300 could generate a three dimensional image of the annulus of frame 10. The user could then more readily see the relative alignment of the annulus, valve leaflets and the implant 1.

The implant 1 or other implants may be delivered, positioned and anchored to reshape the valve annulus or replace the entire valve. Particular embodiments of delivery methods are described in detail herein with reference to the figures.

Generally, the method includes advancing a deployment catheter, such as the delivery catheters described herein, to a deployment site in a heart, with the deployment catheter releasably carrying the implant, such as the implant 1 or other implants including heart valve replacements having valve leaflets. The implant has at least one tissue anchor, such as the anchors described herein. An imaging element, such as the ICE or ultrasound catheters described herein, is positioned in the heart adjacent the implant. A relationship is visualized between the tissue anchor and an anatomical landmark in the heart, and the implant is attached by driving the tissue anchor into tissue in the heart.

In some embodiments, the method generally includes advancing a distal end of a delivery catheter, such as the delivery catheters described herein, proximate the cardiac valve annulus in the heart. The implant, such as the implant 1 or other implants including heart valve replacements having valve leaflets or Mitral valve leaflet repair devices, is advanced through the distal end of the delivery catheter proximate the cardiac valve annulus. A distal end of an ultrasound catheter, such as the ICE or other ultrasound catheters described herein, is advanced proximate the cardiac valve annulus. The distal end of the ultrasound catheter includes one or more ultrasonic transducers. An ultrasound image is captured, the image being of the implant and the cardiac valve annulus, and captured with the one or more ultrasonic transducers, and the implant is anchored to the cardiac valve annulus. The images may be used to verify the position of, and/or re-position, the anchors before driving the anchors into the cardiac tissue.

These are general descriptions of some embodiments of methods that may be performed. Particular embodiments of delivering an annulus re-sizing implant are described with respect to FIGS. 4A-4E, and of delivering a heart valve replacement implant are described with respect to FIGS. 5A-5C.

Figure 4A:
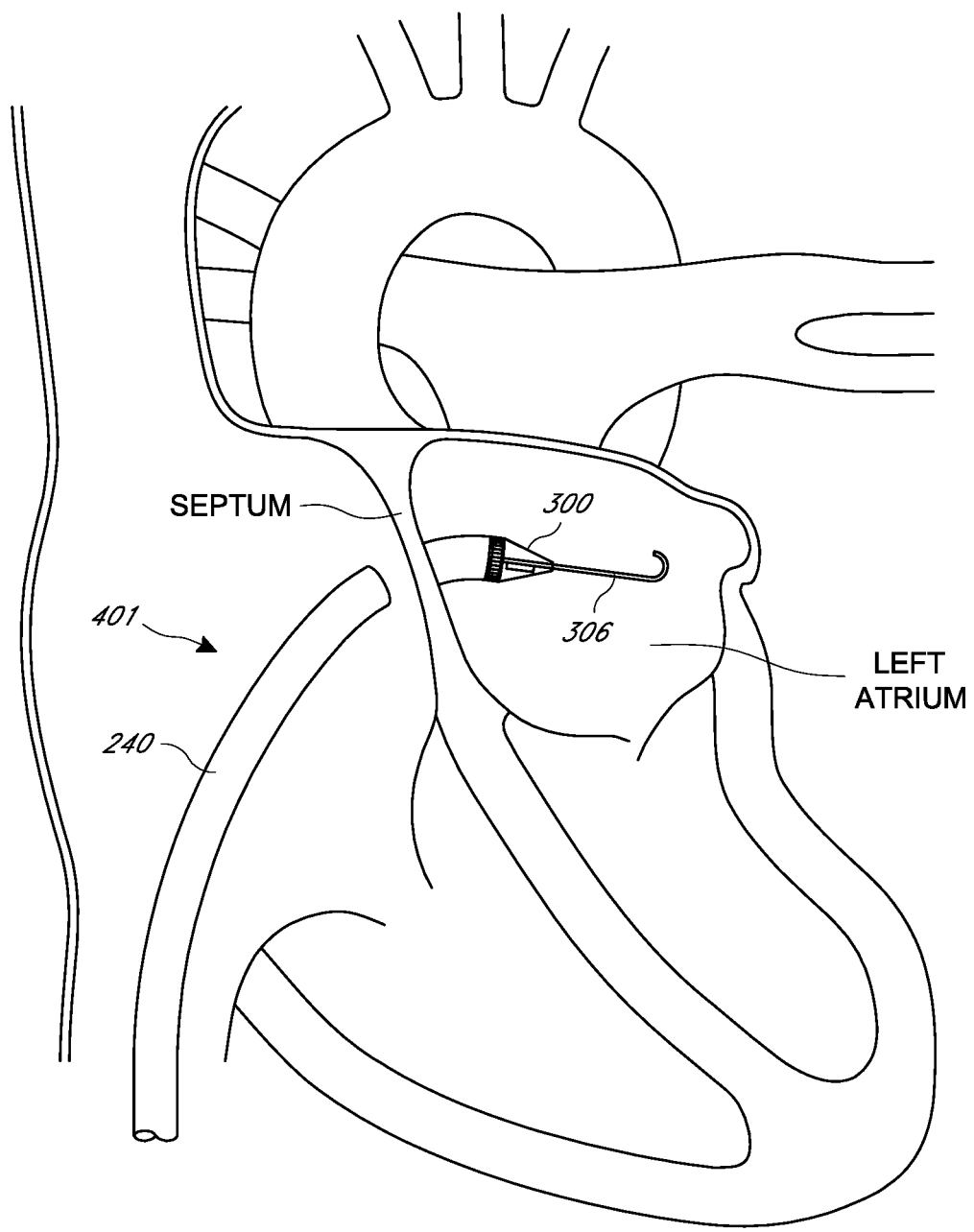
FIGS. 4A through 4E are sequential perspective views of an embodiment of a delivery system with imaging capability showing an embodiment of a method for the delivery, positioning and anchoring of an embodiment of an implant for resizing the native valve annulus.

As shown in FIG. 4A, the implant 1 may be inserted into the heart using a delivery system 401. The implant 1 may be inserted using the delivery system 401 via access to the vasculature of the leg, in particular the femoral vein or the iliac vein. The system 401 may include the various implants, catheters and other features described herein, for example the implant 1, a deployment catheter such as the delivery catheter 240, an imaging element such as the ICE catheter 300 and/or transducers thereon, the guidewire 306, etc. The system 401 may include any of the implants described herein, for example implants including valve annulus reshaping devices or valve replacements that include valve leaflets. The system 401 is then advanced across the septum separating the upper chambers of the heart.

Figure 4B:
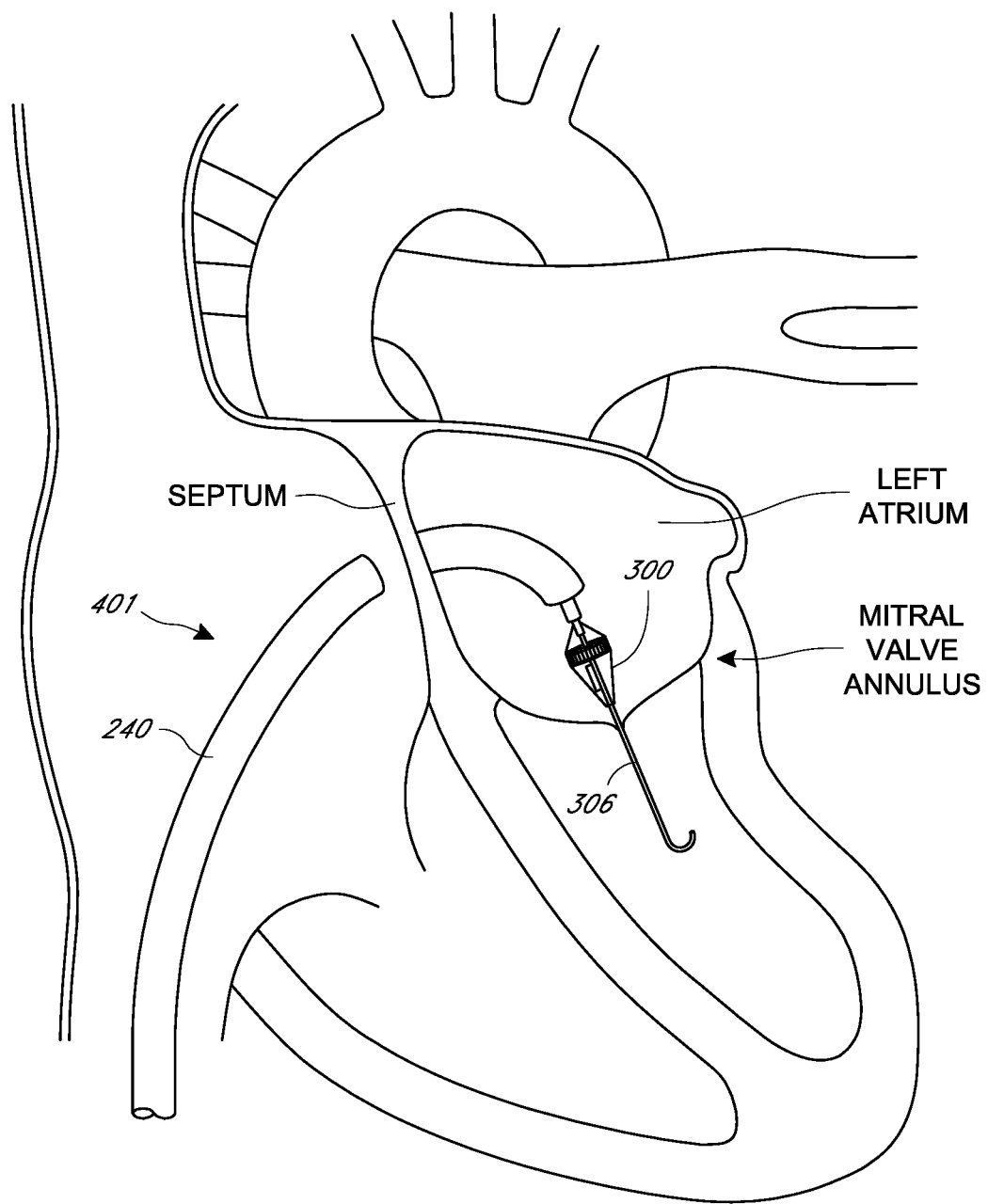
Figure 4C:
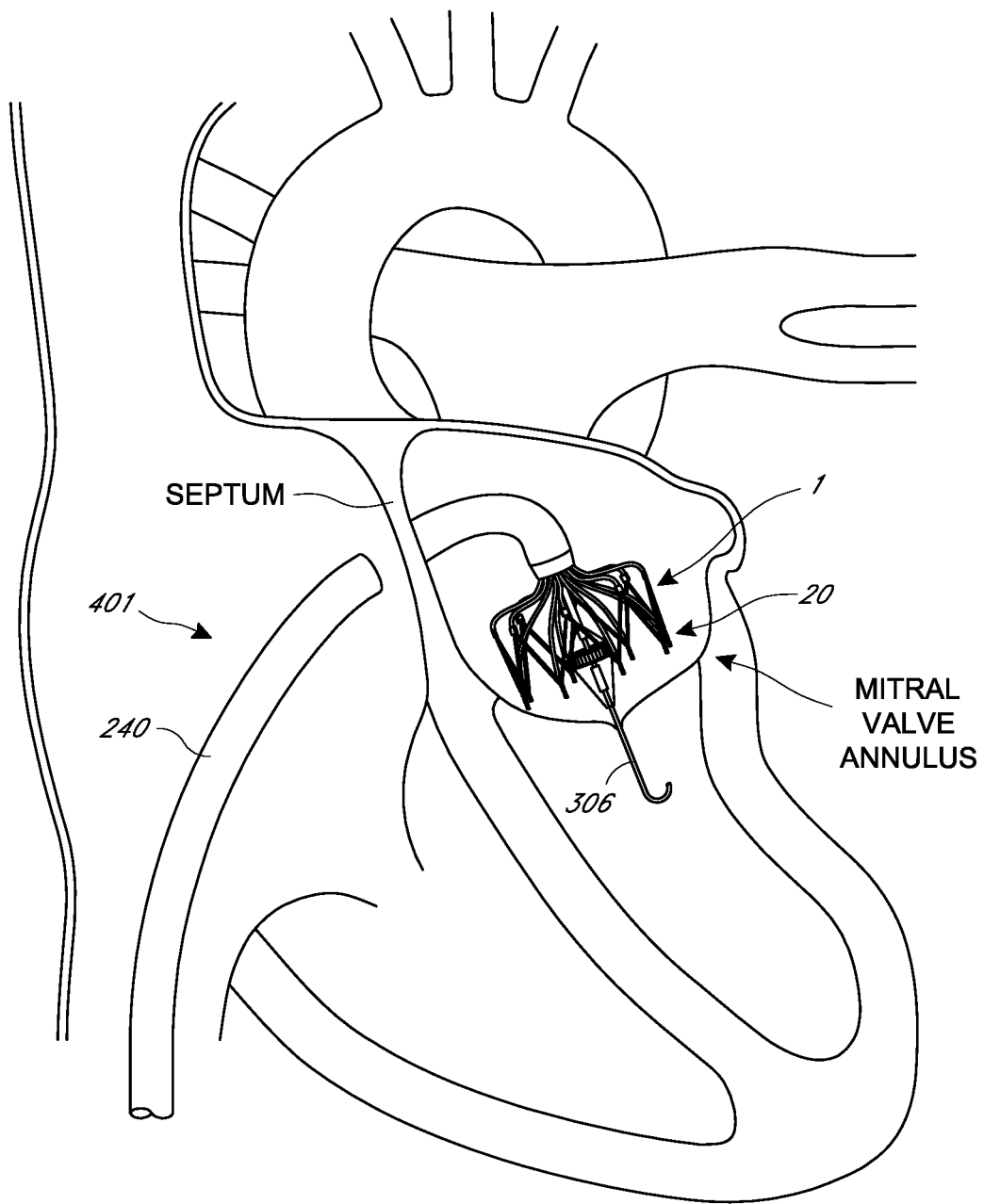

As shown in FIG. 4B, the imaging element such as the ICE catheter 300 is advanced to a position above the heart valve annulus, for example, the mitral valve annulus. FIG. 4C shows the implant 1 expelled, i.e. deployed, from the distal end of the delivery catheter 240 above and proximate to the mitral valve annulus. In some embodiments, the implant 1 may be deployed before the ICE catheter 300.

The ICE catheter 300 may be positioned by advancing the ICE catheter 300 transvascularly along a same access path followed by the delivery catheter 240. The ICE catheter 300 may be positioned by advancing the ICE catheter 300 through a lumen in the delivery catheter 240. In some embodiments, the ICE catheter 300 may be positioned by advancing the ICE catheter 300 transvascularly along a different path than that followed by the delivery catheter 240. As further shown in FIG. 4B, the guidewire 306 may extend through the annulus and into the left ventricle.

In some embodiments, the delivery system 401 may be used to treat the tricuspid valve. For example, the delivery system 401 may be inserted for access through the jugular vein whereby the system 401 is then advanced down the superior vena cava and into the right atrium proximate and above the tricuspid valve annulus.

In some embodiments, the ICE catheter 300 is positioned by directing the ICE catheter 300 to a predetermined relationship with the deployment catheter 240 using an alignment structure, such as the centering frame 32 or 280. In some embodiments, the ICE catheter 300 is centered within the implant 1 using the alignment structure. In some embodiments, an alignment arm, such as the radial centering arm 34, of the alignment structure is inclined with respect to a longitudinal axis of the deployment catheter 240.

In some embodiments, the deployment catheter has a central longitudinal axis and the ICE catheter 300, for example the distal end and/or a transducer thereon, is deflected away from the central longitudinal axis. In some embodiments, the method comprises deflecting the ICE catheter 300 in the direction of one or more of the tissue anchors 20. In some embodiments, a first image of a first anchor 20 is captured, the ICE catheter 300 or portion thereof is then repositioned, and then a second image of a second anchor 20 is captured. In some embodiments, the repositioning step comprises rotating the ICE catheter 300 about an axis. In some embodiments, the repositioning step comprises rotating the ICE catheter 300 about an axis using a rotational drive mechanism. In some embodiments, the repositioning step comprises manually rotating the ICE catheter 300 about the axis. In some embodiments, the ICE catheter 300 carries the imaging element such as a transducer, and the imaging element is rotated, deflected, etc. as described. In some embodiments, a proximal engagement structure on the ICE catheter 300 is locked to a complementary engagement structure on the delivery catheter 240.

Figure 4D:
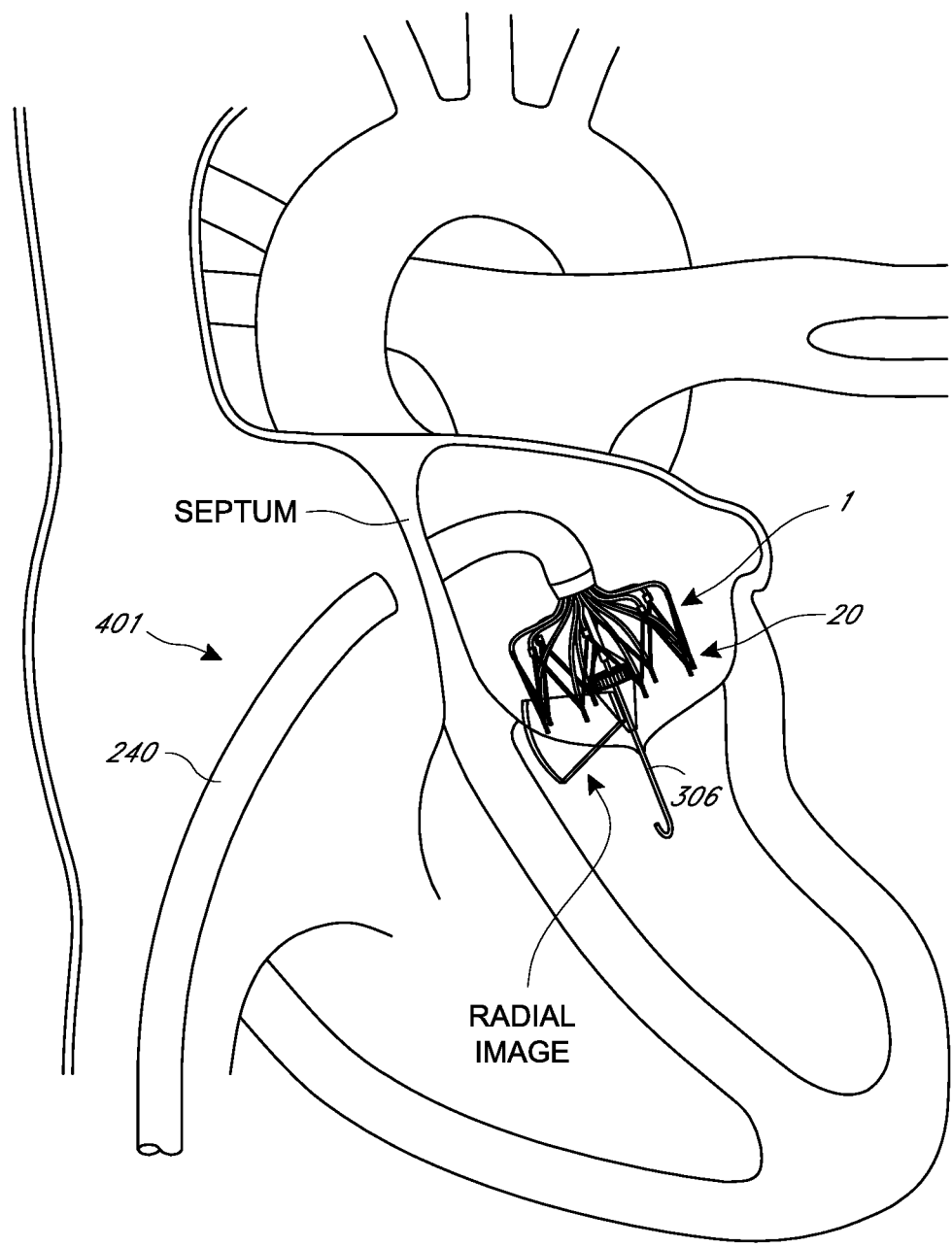

As shown in FIG. 4D, at least one radial image is taken with the ICE catheter 300. A series of radial images may be taken. The radial images are used to properly position the anchors 20 for insertion into the mitral valve annulus tissue. The anchors 20 may be confirmed to be in the proper position, orientation, etc. and driven into the cardiac tissue, for example by rotating the anchors 20. In some embodiments, the implant is attached by driving at least two anchors into tissue in the heart. In some embodiments, the implant is attached by driving at least six anchors into tissue in the heart. In some embodiments, the implant is attached by driving at least eight anchors into tissue in the heart. Other amounts of the anchors may be used as well.

In some embodiments, the distal end of the ICE catheter 300 is rotated proximate the cardiac valve annulus to a plurality of rotational positions, and a series of ultrasound images are captured of the implant 1 and the cardiac valve annulus at the plurality of rotational positions.

Figure 4E:
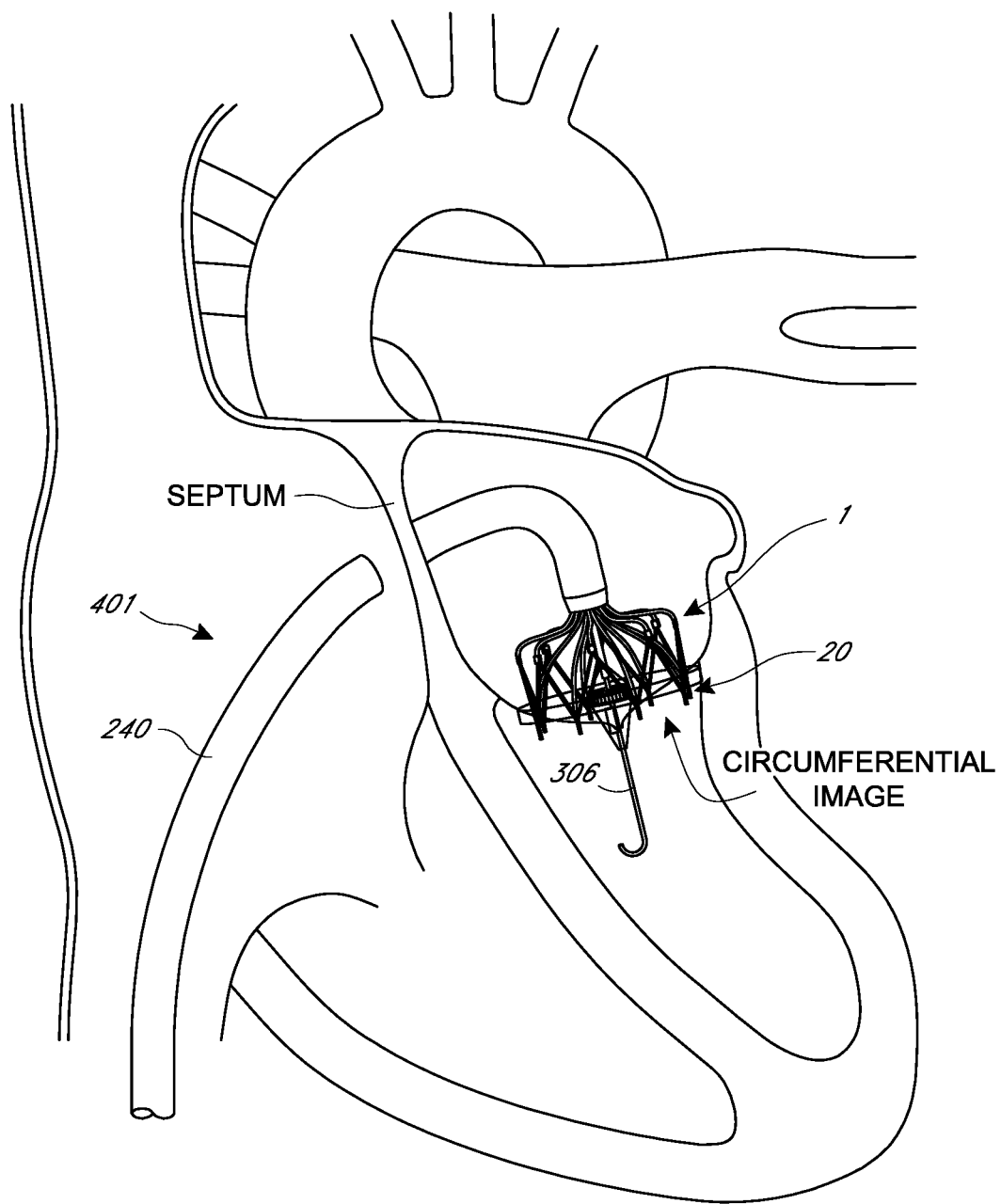

As shown in FIG. 4E, a circumferential image is captured. In some embodiments, multiple circumferential images may be taken. The circumferential image is taken after the one or more radial images. In some embodiments, the circumferential image may be taken prior to the radial imaging. The circumferential image may be used to confirm that all anchors 20 are appropriately placed and anchored in the mitral valve annulus tissue above the mitral valve leaflets. If one or more anchors 20 are not positioned or anchored properly, they can be manipulated, for example rotationally retracted, repositioned and re-anchored, prior to removal of the driver tubes. In addition, a circumferential image can be taken prior to anchoring to confirm location of the lower crowns 16 of the frame 10 of the implant 1. The radial and/or circumferential images may be used to visualize various anatomical features of the heart, such as the heart valve annulus, the heart valve, valve leaflets, the Mitral valve, the Tricuspid valve, and/or other features. In addition or alternatively, the radial and/or circumferential images may be used to visualize various features of the delivery system 401, such as the implant 1, the anchors 20, etc. The implant 1 may be released from the delivery catheter 240 following capturing the circumferential image.

Figure 5A:
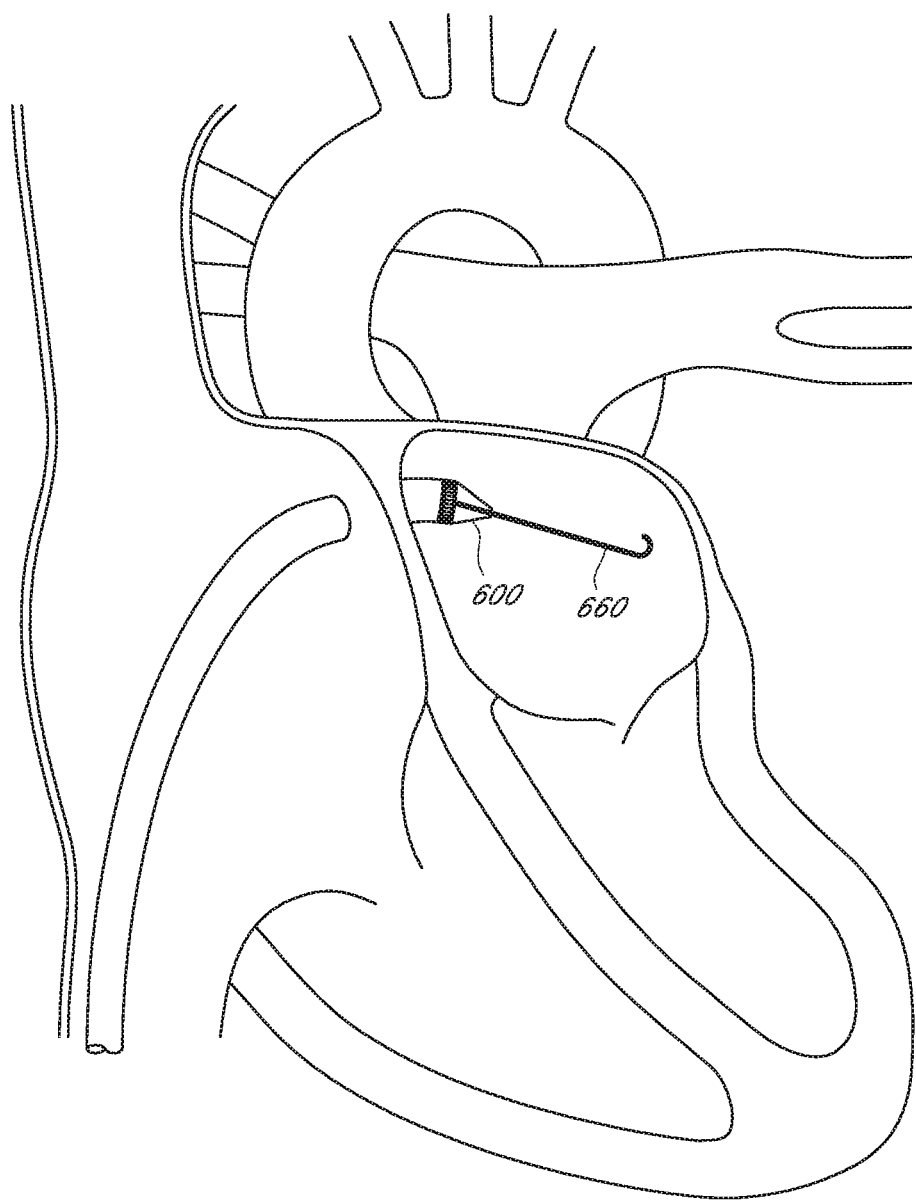
FIGS. 5A-5C are sequential perspective views of an embodiment of a delivery system with imaging capability showing an embodiment of a method for the delivery, positioning and anchoring of an embodiment of a replacement heart valve implant.
Figure 5B:
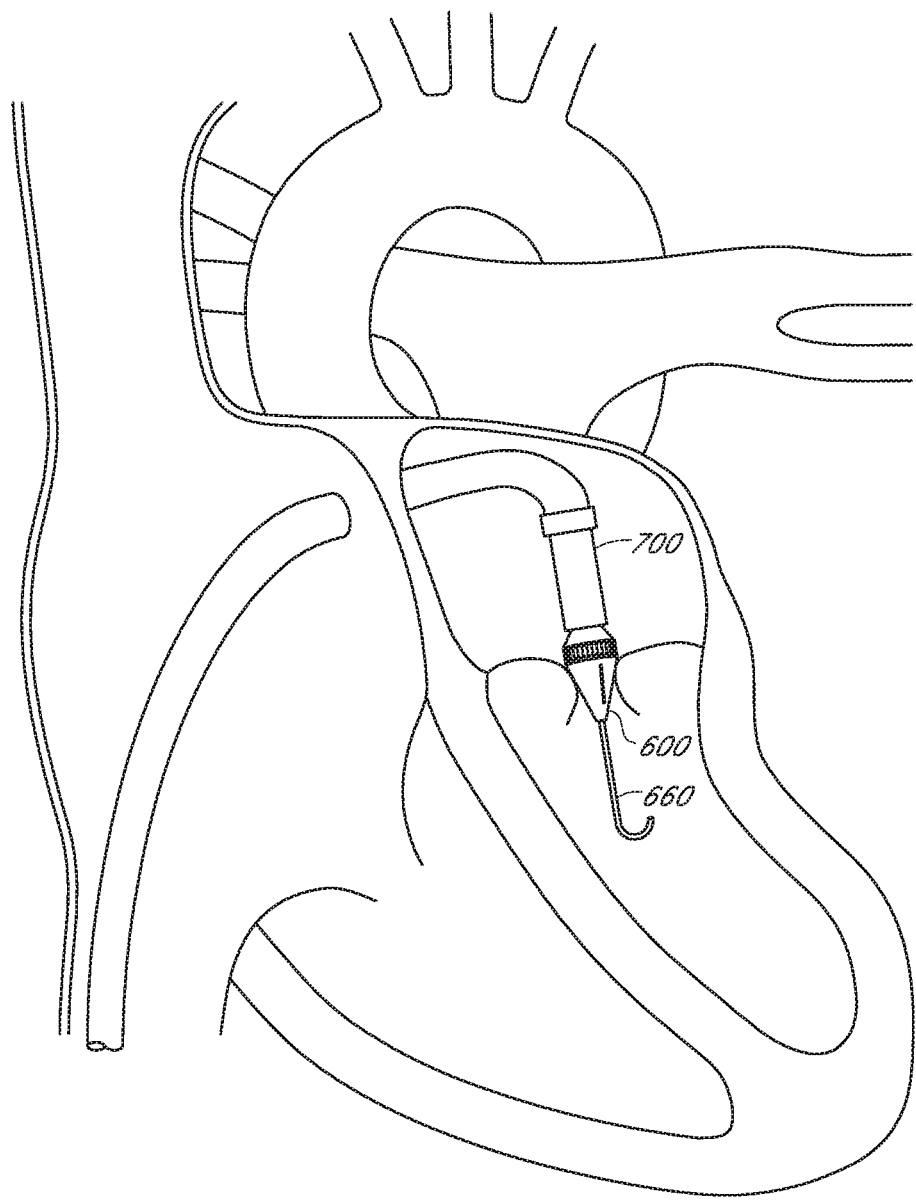
Figure 5C:
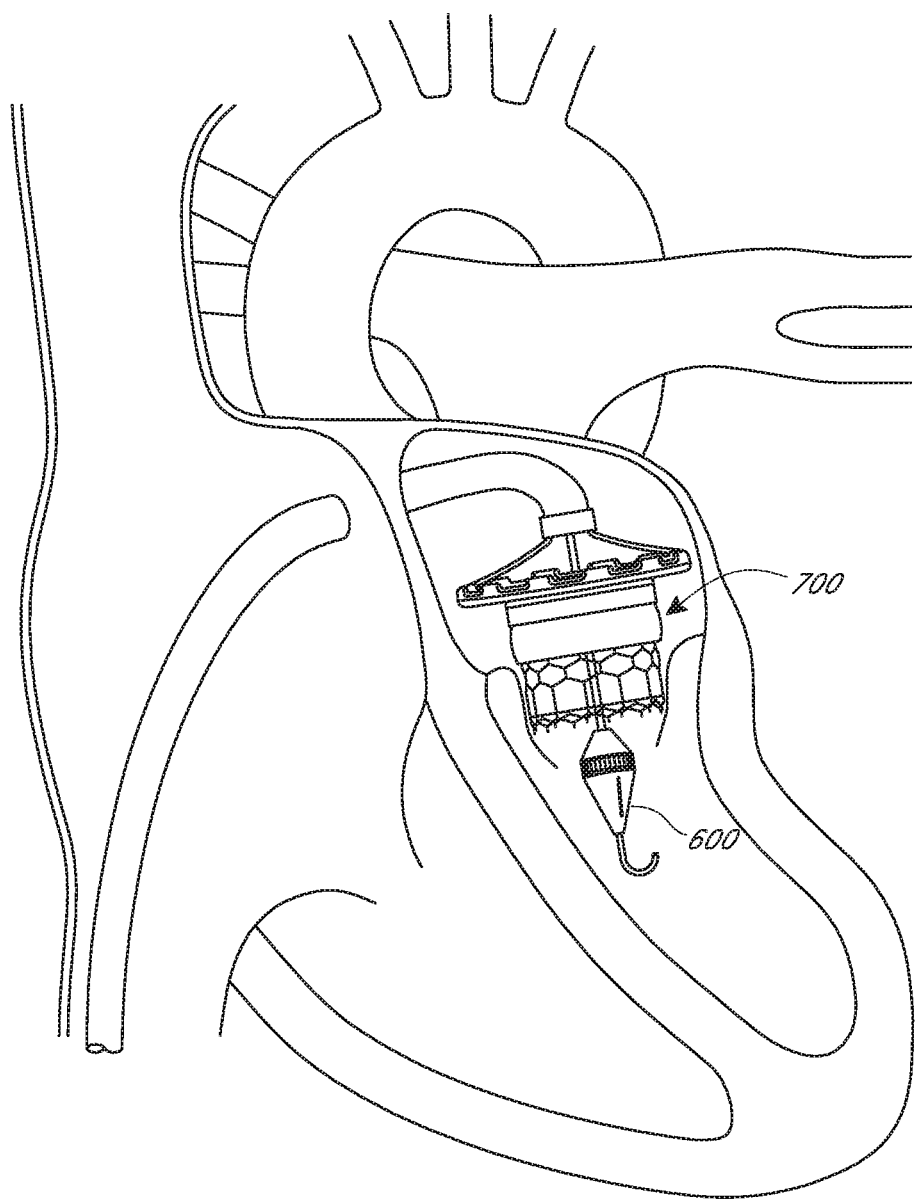

FIGS. 5A-5C are sequential perspective views of an embodiment of a delivery system with imaging capability showing an embodiment of a method for the delivery, positioning and anchoring of an artificial or replacement heart valve 700. The methods described with respect to FIGS. 5A-5C of delivering the replacement heart valve 700 may incorporate any of the features of the delivery method described with respect to FIGS. 4A-4E regarding delivery of the implant 1.

FIGS. 5A-5C show an ultrasound catheter 600 having a guidewire 660 used to guide or assist in the delivery and positioning of the replacement heart valve 700. The replacement heart valve 700 may be a variety of suitable heart Mitral or Tricuspid heart valve replacements, such as the Edwards Lifesciences Fortis or the Medtronic Twelve transcatheter mitral valve. In some embodiments, the replacement heart valve 700 with valve leaflets may be delivered with the various ultrasound systems described herein. The delivery system is inserted via access to the vasculature of the leg, in particular the femoral vein or the iliac vein. The system is then advanced across the atrial-septal wall separating the upper chambers of the heart, as shown in FIG. 5A. The ultrasound catheter 600 is advanced to a position above the heart valve annulus, or more specifically, the mitral valve annulus, as shown in FIG. 5B. FIG. 5C shows the valve 700 expelled from the delivery catheter across the mitral valve, excluding and replacing the function of the native valve. The method shown in FIGS. 5A-5C may incorporate other features described herein, such as those described with respect to FIGS. 4A-4E, for example the various imaging features, various other implants, other access points to the heart, etc.

Relatively large diameter catheter shafts are described herein that may be used to deliver the ring-like implants, such as the implant 1, or valve replacements, such as the valve 700, described herein. These large diameter catheter shafts may include features that mitigate or eliminate the tendency to kink, wrinkle or tear when attempting a sharp bend radius. FIGS. 6A through 9 show various embodiments of sections of steerable catheters that improve the catheter's ability to maneuver tight bends to a position above and proximate and/or into the mitral valve annulus or tricuspid valve annulus.

Figure 6A:
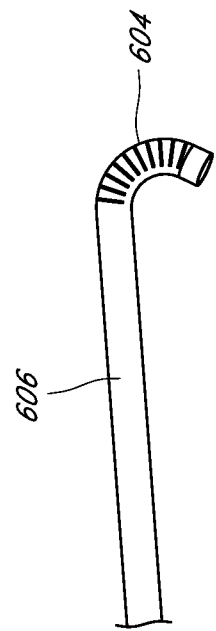
FIGS. 6A and 6B are side views of an embodiment of a steerable catheter shown in straight and flexed states, respectively, that may be used in the various systems and methods described herein.
Figure 6B:
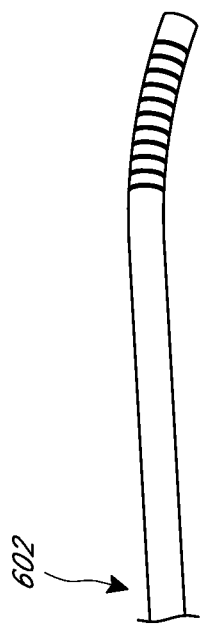

FIGS. 6A and 6B show a steerable catheter 602 in somewhat straight and flexed states, respectively. The steerable catheter 602 may be used in the various delivery systems and methods described herein. The steerable catheter 602 has a distal section 604 and intermediate section 606. The intermediate section 606 may take the form of a shaft section reinforced with a braid or slotted tubing.

Figure 7A:
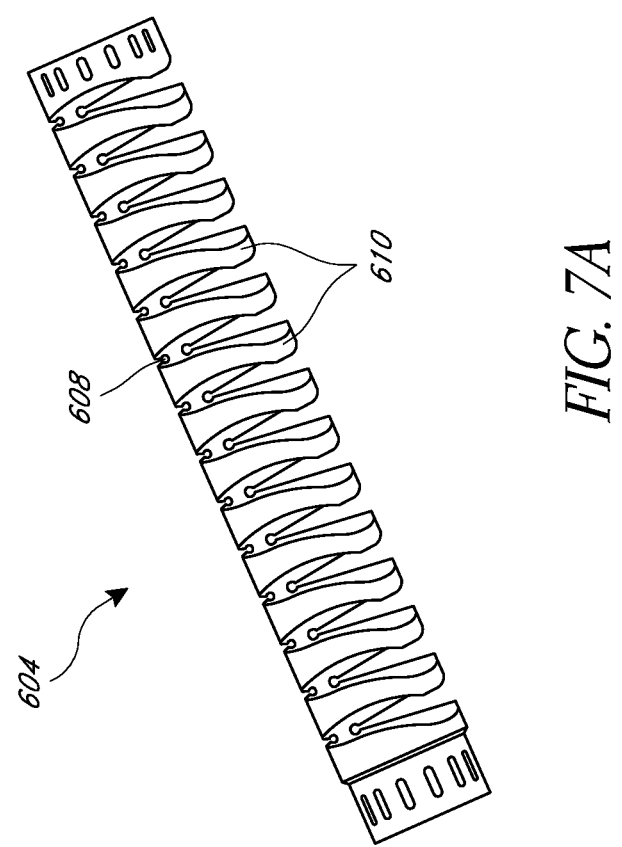
FIGS. 7A and 7B are side views of an embodiment of a distal section of a steerable catheter having a spine that may be used in the various systems and methods described herein.
Figure 7B:
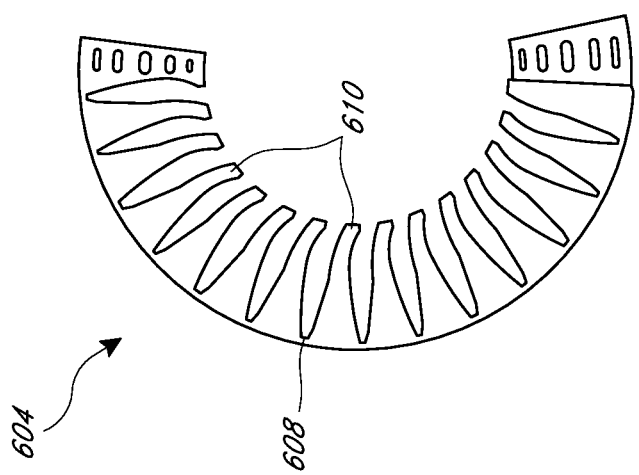

FIGS. 7A and 7B depict an embodiment of the distal section 604 that may be used with the steerable catheter 602, shown in straight and flexed states, respectively. The distal section 604 has a single spine 608 running along its outer curve, and a series of support ribs 610 formed or cut into the inner curve. The distal section 604 may be formed of a flexible metal tube, such as nitinol. The distal section 604 may incorporate pull wires for control of the delivery system. Alternatively, the pull wire may be looped around the distal section's distal tip and back toward the proximal part of the catheter 602. The support ribs 610, with voids therebetween, allow the distal section 604 to achieve a tight bend radius. This flexed state of the distal section 604 is realized with minimal protrusion of the support ribs 610 into the inner diameter or outer diameter of the distal section 604. Moreover, the spine 608 provides a smooth surface on the outer curve of the distal section 604 minimizing friction or interference with heart tissue during delivery and positioning of the catheter and implant.

Figure 8B:
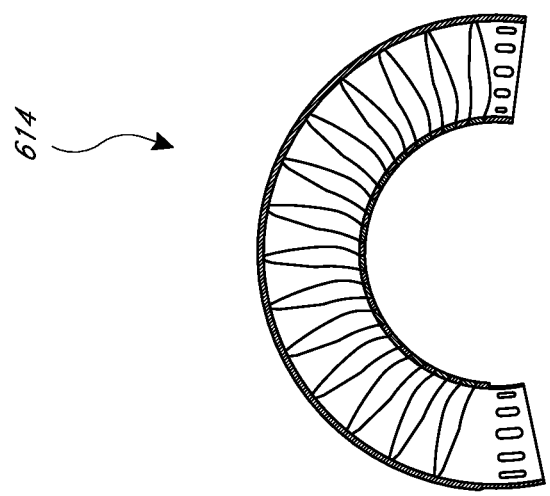
FIGS. 8A and 8B are side views of another embodiment of a distal section of a steerable catheter having a thin film that may be used in the various systems and methods described herein.
Figure 8A:
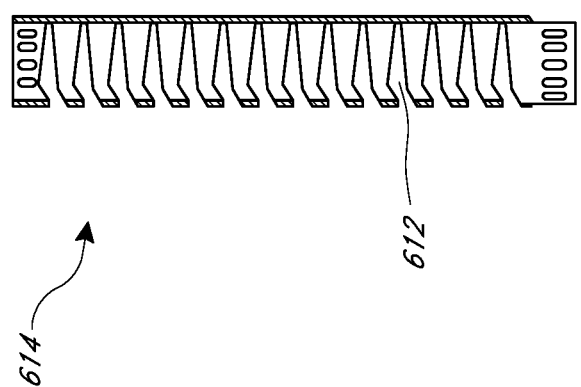

FIGS. 8A and 8B illustrate another embodiment of a distal section 614 that may be used with the steerable catheter 602. Here, the distal section 614 may be a flexible metal tube that is wrapped or encased in a thin film 612 or polymeric material such as Teflon, pTfe, nylon or other thin material. This thin film 612 encapsulation does not restrict the flexibility of the distal section 614 but does provide for smoother delivery and transition into and out of a guide catheter. The thin film 612 may be stretchable or designed to fold in on itself, somewhat similar to an accordion, when flexed as shown in FIG. 8B.

Figure 9:
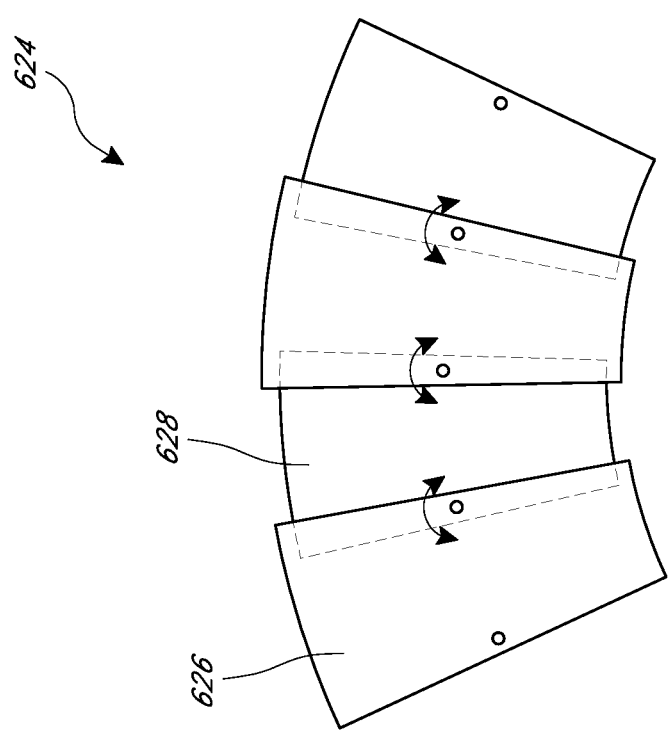
FIG. 9 is a side view of another embodiment of a distal section of a steerable catheter having nesting elements that may be used in the various systems and methods described herein.

FIG. 9 shows another embodiment of a distal section 624 that may be used with the steerable catheter 602. Here, distal section 624 comprises a series of larger elements 626 and smaller elements 628. The smaller elements 628 nest within the larger elements 626. All elements may slide over one another. When the distal section 624 is in a straight state, the metal elements are most overlapped. As the distal section 624 is actuated towards the flexed state, as shown for example in FIG. 9, there may be progressively less overlap of the elements particularly on the outer curve of the distal section 624.

The embodiments of the distal and intermediate sections of the catheter 602 are intended for use in the delivery and implant of both the ring-like embodiments and the replacement valve embodiments described herein. In treating the mitral valve, for example, once the catheter is passed through the septum separating the right and left atria, it is guided slightly upwardly towards the upper reaches of the left atrial chamber. It is then bent significantly in a direction downward towards the mitral annulus, aligning the distal end and the implant with the mitral annulus. The devices, systems and methods described herein allow such bending to occur without kinking or wrinkling which would otherwise impede delivery of the implant.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. An implant delivery system comprising:
   a delivery catheter comprising a proximal end, a distal end and a lumen extending from the proximal end to the distal end, the delivery catheter configured to transluminally position the distal end of the delivery catheter proximate to a valve annulus;
   an implant releasably coupled to the distal end of the delivery catheter, the implant comprising a tubular frame defining an opening, and at least one tissue anchor proximate to said opening;
   an imaging catheter comprising an imaging element at its distal end; and
   an alignment mechanism coupled to the implant and to the imaging catheter and configured to position the imaging catheter relative to the implant for visualization during deployment.

2. The implant delivery system of claim 1, wherein the alignment mechanism further comprises an alignment frame coupled to the frame of the implant.

3. The implant delivery system of claim 1, wherein the alignment mechanism mechanically docks the imaging catheter to the delivery catheter.

4. The implant delivery system of claim 3, wherein the lumen of the delivery catheter extends along a longitudinal axis and the imaging element is aligned with the longitudinal axis of the delivery catheter.

5. The implant delivery system of claim 3, wherein the lumen lies along a longitudinal axis of the delivery catheter and the imaging element diverges from the longitudinal axis of the delivery catheter.

6. The implant delivery system of claim 5, wherein the alignment mechanism diverts the imaging element towards the at least one tissue anchor.

7. The implant delivery system of claim 1, wherein the alignment mechanism comprises the lumen of the delivery catheter.

8. The implant delivery system of claim 1, wherein the imaging catheter is configured for advancement of the imaging element through the distal end of the lumen of the delivery catheter into the opening of the tubular frame.

9. The implant delivery system of claim 1, wherein the imaging element comprises one or more ultrasonic transducers.

10. The implant delivery system of claim 9, wherein the one or more ultrasonic transducers includes a radial ultrasonic transducer.

11. The implant delivery system of claim 1, wherein the imaging catheter comprises an intravascular cardiac echography (ICE) catheter.

12. The implant delivery system of claim 1, wherein the alignment mechanism centers the imaging catheter within the implant.

13. The implant delivery system of claim 1, wherein the delivery catheter is configured to transluminally position the distal end of the delivery catheter proximate to one of a mitral valve annulus and a tricuspid valve annulus, and the tubular frame is configured to be anchored to the one of a mitral valve annulus and a tricuspid valve by the at least one tissue anchor extending from a distal end of the tubular frame.

14. An implant comprising:
    a series of struts defining a tubular frame and an axis and forming a plurality of upper crowns and lower crowns;
    a plurality of anchors coupled with at least some of the plurality of lower crowns of the tubular frame and configured to translate axially relative to the tubular frame to engage cardiac tissue proximate the cardiac valve annulus; and
    an alignment mechanism for an imaging catheter, the alignment mechanism being coupled to the tubular frame and configured to position an imaging element of the imaging catheter at a predetermined location relative to the tubular frame.

15. The implant of claim 14, further comprising a plurality of collars at least partially surrounding the upper crowns and configured to translate axially relative to the tubular frame to adjust a width of the implant.

16. The implant of claim 14, wherein the alignment mechanism is configured to enable rotation of the imaging catheter within the tubular frame.

17. The implant of claim 14, wherein the alignment mechanism includes at least one strut coupled to the tubular frame configured to center the imaging catheter within the tubular frame when the tubular frame is in an expanded state.

18. The implant of claim 14, wherein the tubular frame is sized to surround at least a portion of a mitral valve annulus.

19. The implant of claim 14, wherein the tubular frame is sized to surround at least a portion of a tricuspid valve annulus.

20. A cardiac valve implant delivery system comprising:
    a delivery catheter comprising a proximal end, a distal end and a lumen extending from the proximal end to the distal end, the delivery catheter configured to transluminally position the distal end of the delivery catheter proximate to a cardiac valve annulus;
    an implant releasably coupled to the distal end of the delivery catheter, the implant comprising a tubular frame comprised of a series of struts joined to form a plurality of upper and lower crowns;
    a plurality of anchors coupled with the lower crowns of the tubular frame and configured to translate axially relative to the tubular frame to engage cardiac tissue proximate the cardiac valve;
    an imaging catheter comprising at least one imaging element rotatably disposed within the tubular frame; and
    an alignment mechanism coupled to the tubular frame and the imaging catheter and configured to position the imaging elements of the imaging catheter within the tubular frame to enable visualization of the plurality of anchors during deployment of a cardiac valve implant.

* * * * *